US011084770B2

(12) United States Patent
Black et al.

(10) Patent No.: US 11,084,770 B2
(45) Date of Patent: *Aug. 10, 2021

(54) CANNABIS EXTRACTS

(71) Applicant: Treehouse Biotech, Inc., Boulder, CO (US)

(72) Inventors: Jacob Black, New Haven, CT (US); Ryan Beigie, Littleton, CO (US); Alex Mateo, Lakewood, CO (US)

(73) Assignee: Treehouse Biotech, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/266,326

(22) Filed: Feb. 4, 2019

(65) Prior Publication Data

US 2019/0270691 A1 Sep. 5, 2019

Related U.S. Application Data

(63) Continuation of application No. 15/834,826, filed on Dec. 7, 2017, now Pat. No. 10,239,808.

(Continued)

(51) Int. Cl.
| | |
|---|---|
| *C07C 37/72* | (2006.01) |
| *B01D 15/32* | (2006.01) |
| *G01N 30/02* | (2006.01) |
| *C07C 39/23* | (2006.01) |
| *C07D 311/78* | (2006.01) |
| *C07B 63/00* | (2006.01) |
| *A61K 31/352* | (2006.01) |
| *A61K 36/185* | (2006.01) |

(Continued)

(52) U.S. Cl.
CPC ............ *C07C 37/72* (2013.01); *A61K 31/352* (2013.01); *A61K 36/185* (2013.01); *B01D 15/322* (2013.01); *B01D 15/325* (2013.01); *C07B 63/00* (2013.01); *C07C 37/004* (2013.01); *C07C 39/23* (2013.01); *C07D 311/78* (2013.01); *G01N 30/02* (2013.01); *G01N 30/88* (2013.01); *A61K 2236/00* (2013.01); *C07C 2601/16* (2017.05); *G01N 30/90* (2013.01); *G01N 2030/027* (2013.01)

(58) Field of Classification Search
CPC ............ G01N 30/02; G01N 2030/027; B01D 15/322; B01D 15/325; C07C 37/72
See application file for complete search history.

(56) References Cited

U.S. PATENT DOCUMENTS

| | | |
|---|---|---|
| 2,304,669 A | 12/1942 | Adams |
| 2,419,934 A | 5/1947 | Adams |

(Continued)

FOREIGN PATENT DOCUMENTS

| | | |
|---|---|---|
| AU | 2000012348 | 7/2000 |
| AU | 2000012349 | 8/2000 |

(Continued)

OTHER PUBLICATIONS

PCT International Search Report and Written Opinion in International Application PCT/US2019/016182, dated May 27, 2019, 17 pages.

(Continued)

*Primary Examiner* — Yate' K Cutliff

(57) ABSTRACT

A method is provided for removing THC from raw cannabis oil.

11 Claims, 18 Drawing Sheets

Related U.S. Application Data

(60) Provisional application No. 62/431,209, filed on Dec. 7, 2016.

(51) Int. Cl.
    *C07C 37/00*     (2006.01)
    *G01N 30/88*     (2006.01)
    *G01N 30/90*     (2006.01)

(56) References Cited

U.S. PATENT DOCUMENTS

| | | |
|---|---|---|
| 3,576,887 A | 4/1971 | Hughes et al. |
| 3,734,930 A | 5/1973 | Razdan et al. |
| 5,137,626 A | 8/1992 | Parry et al. |
| 5,252,490 A | 10/1993 | Elsohly et al. |
| 5,338,753 A | 8/1994 | Burstein et al. |
| 5,633,357 A | 5/1997 | Tius et al. |
| 5,847,128 A | 12/1998 | Martin et al. |
| 6,365,416 B1 | 4/2002 | Elsohly |
| 6,403,126 B1 | 6/2002 | Webster |
| 6,730,519 B2 | 5/2004 | Elsohly |
| 7,700,368 B2 * | 4/2010 | Flockhart .............. C07D 311/80 436/177 |
| 8,343,553 B2 | 1/2013 | Hospodor |
| 8,445,034 B1 | 5/2013 | Coles, Jr. |
| 8,497,299 B2 | 7/2013 | Mechoulam et al. |
| 8,673,368 B2 * | 3/2014 | Guy ..................... A61K 36/185 424/725 |
| 8,771,760 B2 | 7/2014 | Guy et al. |
| 8,846,409 B2 | 9/2014 | Flockhart et al. |
| 8,859,016 B2 | 10/2014 | Pritchett |
| 8,895,078 B2 | 11/2014 | Mueller |
| 8,980,941 B2 | 3/2015 | Hospodor |
| 9,169,455 B2 | 10/2015 | Hamler et al. |
| 9,199,960 B2 | 12/2015 | Ferri |
| 9,376,367 B2 | 6/2016 | Herkenroth et al. |
| 9,394,510 B2 | 7/2016 | Peet et al. |
| 9,526,792 B1 | 12/2016 | Degeeter |
| 9,603,887 B2 | 3/2017 | Kelly |
| 9,655,936 B2 | 5/2017 | Ruben et al. |
| 9,718,065 B1 | 8/2017 | Cilia |
| 9,744,151 B2 | 8/2017 | Gutman et al. |
| 9,808,494 B2 | 11/2017 | Barringer |
| 9,814,775 B2 | 11/2017 | Rossi et al. |
| 9,815,810 B1 | 11/2017 | Ogilvie et al. |
| 9,895,404 B1 | 2/2018 | Baskis |
| 9,901,607 B2 | 2/2018 | Silen |
| 9,913,868 B1 | 3/2018 | Alfiere |
| 9,919,241 B1 | 3/2018 | Auerbach et al. |
| 9,937,147 B2 | 4/2018 | DeGeeter |
| 9,937,218 B2 | 4/2018 | Towle |
| 9,950,275 B1 | 4/2018 | Ruben et al. |
| 9,956,174 B1 | 5/2018 | Nordahl |
| 9,974,820 B2 | 5/2018 | Ablett |
| 9,974,821 B2 | 5/2018 | Kennedy |
| 9,981,203 B2 | 5/2018 | Shuja |
| 10,004,684 B2 | 6/2018 | Whittle et al. |
| 10,011,804 B2 | 7/2018 | Mancosky |
| 10,016,360 B1 | 7/2018 | Elbogen et al. |
| 10,028,987 B1 | 7/2018 | Pillsbury |
| 10,105,343 B2 | 10/2018 | Kubby |
| 10,137,161 B2 | 11/2018 | Kolsky |
| 10,155,176 B1 | 12/2018 | Feuer et al. |
| 10,179,683 B2 | 1/2019 | Whittle |
| 10,188,628 B1 | 1/2019 | Kershman et al. |
| 10,189,762 B1 | 1/2019 | Oroskar et al. |
| 10,195,159 B2 | 2/2019 | Whittle et al. |
| 10,206,888 B2 | 2/2019 | Vu et al. |
| 10,207,199 B2 | 2/2019 | Nadal Roura |
| 10,213,788 B2 | 2/2019 | Bates |
| 10,214,753 B2 | 2/2019 | Peet et al. |
| 10,226,496 B2 | 3/2019 | Sekura et al. |
| 10,238,705 B2 | 3/2019 | Speier |
| 10,238,706 B1 | 3/2019 | Nahtigal |
| 10,238,745 B2 | 3/2019 | Finley et al. |
| 10,239,808 B1 | 3/2019 | Black et al. |
| 10,245,525 B1 | 4/2019 | Ko |
| 10,246,431 B2 | 4/2019 | Changoer et al. |
| 10,265,295 B2 | 4/2019 | Sorbo et al. |
| 2003/0017216 A1 | 1/2003 | Schmidt et al. |
| 2003/0050334 A1 | 3/2003 | Murty et al. |
| 2006/0078955 A1 | 4/2006 | Lin et al. |
| 2006/0135599 A1 | 6/2006 | Symonds et al. |
| 2006/0194761 A1 | 8/2006 | Gu |
| 2007/0077660 A1 | 4/2007 | Glas |
| 2007/0287843 A1 | 12/2007 | Cabaj et al. |
| 2008/0103193 A1 | 5/2008 | Castor et al. |
| 2008/0181942 A1 | 7/2008 | Zajicek |
| 2008/0221339 A1 | 9/2008 | Webster et al. |
| 2008/0312465 A1 | 12/2008 | Souza et al. |
| 2009/0042974 A1 | 2/2009 | Parker et al. |
| 2009/0197941 A1 | 8/2009 | Guy et al. |
| 2009/0306221 A1 | 12/2009 | Guy et al. |
| 2010/0292345 A1 | 11/2010 | Pertwee |
| 2010/0298579 A1 | 11/2010 | Steup et al. |
| 2011/0171300 A1 | 7/2011 | Bhatarah et al. |
| 2011/0257256 A1 | 10/2011 | Fuchs et al. |
| 2012/0144523 A1 | 6/2012 | Page et al. |
| 2013/0079531 A1 | 3/2013 | Barringer |
| 2013/0295172 A1 | 11/2013 | Freeman |
| 2014/0057251 A1 | 2/2014 | McKeman |
| 2014/0243405 A1 | 8/2014 | Whalley et al. |
| 2014/0271940 A1 | 9/2014 | Wurzer |
| 2014/0287067 A1 | 9/2014 | Velasco Diez et al. |
| 2015/0057342 A1 | 2/2015 | Koren et al. |
| 2015/0083146 A1 | 3/2015 | Goldman et al. |
| 2015/0126754 A1 | 5/2015 | Fernandez Cid et al. |
| 2015/0203434 A1 | 7/2015 | Flockhart et al. |
| 2015/0258153 A1 | 9/2015 | Rosenblatt et al. |
| 2015/0361469 A1 | 12/2015 | Winnicki |
| 2016/0002579 A1 | 1/2016 | Rosenthal et al. |
| 2016/0018424 A1 | 1/2016 | Lucas et al. |
| 2016/0051510 A1 | 2/2016 | Allen et al. |
| 2016/0058866 A1 | 3/2016 | Sekura et al. |
| 2016/0143972 A1 | 5/2016 | Stebbins et al. |
| 2016/0158299 A1 | 6/2016 | Bohus |
| 2016/0177404 A1 | 6/2016 | McKeman |
| 2016/0228787 A1 | 8/2016 | Payack |
| 2016/0243460 A1 | 8/2016 | Leveson et al. |
| 2016/0279183 A1 | 9/2016 | Hospodor et al. |
| 2016/0298151 A1 | 10/2016 | Butt et al. |
| 2016/0324776 A1 | 11/2016 | Glatzel |
| 2016/0324777 A1 | 11/2016 | Victor et al. |
| 2016/0354561 A1 | 12/2016 | McCullough |
| 2016/0360721 A1 | 12/2016 | De Meijer |
| 2017/0008870 A1 | 1/2017 | Dibble et al. |
| 2017/0021029 A1 | 1/2017 | Raber et al. |
| 2017/0022132 A1 | 1/2017 | Mona, III et al. |
| 2017/0042835 A1 | 2/2017 | Singh |
| 2017/0079933 A1 | 3/2017 | Whittle et al. |
| 2017/0095518 A1 | 4/2017 | Bjorncrantz |
| 2017/0119728 A1 | 5/2017 | DeGeeter |
| 2017/0188605 A1 | 7/2017 | Franklin et al. |
| 2017/0196923 A1 | 7/2017 | Moore |
| 2017/0202896 A1 | 7/2017 | Hugh |
| 2017/0240840 A1 | 8/2017 | Privitera et al. |
| 2017/0252384 A1 | 9/2017 | Goldner |
| 2017/0283837 A1 | 10/2017 | Kavarana et al. |
| 2017/0290869 A1 | 10/2017 | Whittle et al. |
| 2017/0298399 A1 | 10/2017 | Peet et al. |
| 2017/0312652 A1 | 11/2017 | Love |
| 2017/0360861 A1 | 12/2017 | Humphreys et al. |
| 2017/0361525 A1 | 12/2017 | Warner et al. |
| 2017/0368021 A1 | 12/2017 | Atkinson et al. |
| 2018/0016203 A1 | 1/2018 | Raber et al. |
| 2018/0021247 A1 | 1/2018 | Ghalili et al. |
| 2018/0036278 A1 | 2/2018 | Rutz |
| 2018/0059128 A1 | 3/2018 | McDonald et al. |
| 2018/0064772 A1 | 3/2018 | Naheed |
| 2018/0071701 A1 | 3/2018 | Zhang et al. |
| 2018/0078593 A1 | 3/2018 | Naheed |
| 2018/0078874 A1 | 3/2018 | Thomas |
| 2018/0085684 A1 | 3/2018 | Crandall et al. |

(56) References Cited

U.S. PATENT DOCUMENTS

| | | |
|---|---|---|
| 2018/0092953 A1 | 4/2018 | Brazil |
| 2018/0094209 A1 | 4/2018 | Carberry |
| 2018/0098552 A1 | 4/2018 | Bhairam |
| 2018/0099017 A1 | 4/2018 | Jones |
| 2018/0116998 A1 | 5/2018 | Sinai et al. |
| 2018/0125777 A1 | 5/2018 | Lindsay |
| 2018/0140965 A1 | 5/2018 | Flora et al. |
| 2018/0143212 A1 | 5/2018 | Giese et al. |
| 2018/0147247 A1 | 5/2018 | Ivanov |
| 2018/0161285 A1 | 6/2018 | Mukunda et al. |
| 2018/0193399 A1 | 7/2018 | Kariman |
| 2018/0193403 A1 | 7/2018 | George et al. |
| 2018/0200316 A1 | 7/2018 | Bray et al. |
| 2018/0201560 A1 | 7/2018 | Kavarana et al. |
| 2018/0207213 A1 | 7/2018 | McElvany |
| 2018/0221304 A1 | 8/2018 | Small-Howard et al. |
| 2018/0224411 A1 | 8/2018 | Raber et al. |
| 2018/0228854 A1 | 8/2018 | Raderman |
| 2018/0236017 A1 | 8/2018 | Stoops |
| 2018/0237368 A1 | 8/2018 | Keller |
| 2018/0265803 A1 | 9/2018 | Cumings et al. |
| 2018/0271827 A1 | 9/2018 | Heimark et al. |
| 2018/0273501 A1 | 9/2018 | Robertson et al. |
| 2018/0280459 A1 | 10/2018 | Eyal |
| 2018/0282250 A1 | 10/2018 | Rutz et al. |
| 2018/0289665 A1 | 10/2018 | Turner et al. |
| 2018/0293672 A1 | 10/2018 | Johnson |
| 2018/0318361 A1 | 11/2018 | Eyal |
| 2018/0319763 A1 | 11/2018 | Dialer et al. |
| 2018/0333446 A1 | 11/2018 | Shan et al. |
| 2018/0334692 A1 | 11/2018 | Barr et al. |
| 2018/0343901 A1 | 12/2018 | Leo et al. |
| 2018/0344661 A1 | 12/2018 | Finley et al. |
| 2018/0344662 A1 | 12/2018 | Eyal et al. |
| 2018/0344785 A1 | 12/2018 | Robertson |
| 2018/0346866 A1 | 12/2018 | Peet et al. |
| 2018/0353463 A1 | 12/2018 | Winnicki |
| 2018/0361271 A1 | 12/2018 | Galyuk |
| 2018/0362429 A1 | 12/2018 | Zhang et al. |
| 2018/0369714 A1 | 12/2018 | Coffin |
| 2018/0369715 A1 | 12/2018 | Bruining |
| 2018/0369716 A1 | 12/2018 | Robbins et al. |
| 2018/0371507 A1 | 12/2018 | Poulos et al. |
| 2019/0000794 A1 | 1/2019 | Tanaka |
| 2019/0015383 A1 | 1/2019 | Woelfel et al. |
| 2019/0022054 A1 | 1/2019 | Greenbaum et al. |
| 2019/0023680 A1 | 1/2019 | Leahy et al. |
| 2019/0030062 A1 | 1/2019 | Mukunda et al. |
| 2019/0030100 A1 | 1/2019 | Hospodor et al. |
| 2019/0030102 A1 | 1/2019 | Scialdone |
| 2019/0037909 A1 | 2/2019 | Greenbaum et al. |
| 2019/0038995 A1 | 2/2019 | Tucker |
| 2019/0046440 A1 | 2/2019 | Kleidon et al. |
| 2019/0046499 A1 | 2/2019 | Segreti |
| 2019/0054394 A1 | 2/2019 | Hare |
| 2019/0060227 A1 | 2/2019 | Silver |
| 2019/0060381 A1 | 2/2019 | Ballan et al. |
| 2019/0060785 A1 | 2/2019 | Durward |
| 2019/0062144 A1 | 2/2019 | Greenbaum et al. |
| 2019/0070128 A1 | 3/2019 | Guy et al. |
| 2019/0076756 A1 | 3/2019 | Moore |
| 2019/0077782 A1 | 3/2019 | Raber et al. |
| 2019/0077783 A1 | 3/2019 | Koch et al. |
| 2019/0083418 A1 | 3/2019 | Guy et al. |
| 2019/0083902 A1 | 3/2019 | Nevitt |
| 2019/0085279 A1 | 3/2019 | Leo |
| 2019/0085347 A1 | 3/2019 | Sayre et al. |
| 2019/0090515 A1 | 3/2019 | Franklin et al. |
| 2019/0091144 A1 | 3/2019 | McGarrah et al. |
| 2019/0091200 A1 | 3/2019 | Tepper et al. |
| 2019/0099696 A1 | 4/2019 | Ko et al. |
| 2019/0099736 A1 | 4/2019 | Sibal |
| 2019/0105298 A1 | 4/2019 | Eyal |
| 2019/0117617 A1 | 4/2019 | Kariman |
| 2019/0117778 A1 | 4/2019 | Leone-Bay et al. |
| 2019/0231737 A1 | 8/2019 | Black |
| 2019/0307695 A1 | 10/2019 | Colvin |
| 2019/0382325 A1 | 12/2019 | Black |
| 2019/0382326 A1 | 12/2019 | Black |
| 2020/0079715 A1 | 3/2020 | Davis |
| 2020/0101034 A1 | 4/2020 | Leone-Bay |
| 2020/0115306 A1 | 4/2020 | Smeltzer |

FOREIGN PATENT DOCUMENTS

| | | |
|---|---|---|
| AU | 2002218242 | 7/2002 |
| AU | 2002229456 | 3/2003 |
| AU | 2002255150 | 5/2003 |
| AU | 2002319422 | 5/2003 |
| AU | 2002365231 | 9/2003 |
| AU | 2003205844 | 9/2003 |
| AU | 2017334283 | 4/2018 |
| AU | 2017341707 | 4/2018 |
| AU | 2018100837 | 7/2018 |
| AU | 2018253527 | 11/2018 |
| AU | 2017296180 | 1/2019 |
| AU | 2017301239 | 3/2019 |
| AU | 2017313843 | 3/2019 |
| BR | PI 0910426 A2 | 8/2015 |
| BR | 112013012468 A2 | 9/2016 |
| BR | 112016009872 A2 | 8/2017 |
| BR | 112016030944 A2 | 8/2017 |
| BR | 112017007767 A2 | 1/2018 |
| BR | 112017019899 A2 | 6/2018 |
| BR | 112018001310 A2 | 9/2018 |
| BR | 112018005639 A2 | 10/2018 |
| BR | 112018074859 A2 | 12/2018 |
| BR | 112018005423 A2 | 2/2019 |
| CA | 2348695 | 5/2000 |
| CA | 2472561 | 8/2002 |
| CA | 2469490 | 7/2003 |
| CA | 2391454 | 12/2003 |
| CA | 2504743 | 5/2004 |
| CA | 2656698 | 12/2007 |
| CA | 2751741 | 8/2009 |
| CA | 2910206 | 12/2015 |
| CA | 2937471 | 9/2016 |
| CA | 2941961 | 3/2018 |
| CA | 2997850 | 5/2018 |
| CA | 2911168 | 8/2018 |
| CA | 3000255 | 9/2018 |
| CA | 2993834 | 10/2018 |
| CA | 3024431 | 1/2019 |
| CA | 3024645 | 1/2019 |
| CA | 3013573 | 2/2019 |
| CA | 3009554 | 3/2019 |
| CA | 3004544 | 11/2019 |
| CH | 706963 | 3/2014 |
| CN | 1560005 | 1/2005 |
| CN | 100387230 C | 5/2008 |
| CN | 101932314 | 12/2010 |
| CN | 1962665 | 5/2011 |
| CN | 1997636 | 9/2011 |
| CN | 102766128 | 11/2012 |
| CN | 103300073 | 9/2013 |
| CN | 103417593 | 12/2013 |
| CN | 103739585 | 4/2014 |
| CN | 104031736 | 9/2014 |
| CN | 104277917 | 1/2015 |
| CN | 104302193 A | 1/2015 |
| CN | 204111719 | 1/2015 |
| CN | 104447673 | 3/2015 |
| CN | 105505565 | 4/2016 |
| CN | 105535111 | 5/2016 |
| CN | 105935374 | 9/2016 |
| CN | 105943613 | 9/2016 |
| CN | 105943615 | 9/2016 |
| CN | 105943617 | 9/2016 |
| CN | 105943619 | 9/2016 |
| CN | 105963359 | 9/2016 |
| CN | 105997985 | 10/2016 |
| CN | 105998192 | 10/2016 |
| CN | 106074465 | 11/2016 |
| CN | 106074496 | 11/2016 |

(56) References Cited

FOREIGN PATENT DOCUMENTS

| | | |
|---|---|---|
| CN | 106074707 | 11/2016 |
| CN | 106232130 | 12/2016 |
| CN | 106265364 | 1/2017 |
| CN | 106389535 | 2/2017 |
| CN | 106632214 | 5/2017 |
| CN | 106810426 | 6/2017 |
| CN | 106860492 | 6/2017 |
| CN | 206244694 | 6/2017 |
| CN | 107011125 | 8/2017 |
| CN | 107050001 | 8/2017 |
| CN | 107050002 | 8/2017 |
| CN | 107095302 | 8/2017 |
| CN | 107337586 | 8/2017 |
| CN | 107137604 | 9/2017 |
| CN | 107227198 | 10/2017 |
| CN | 107325881 | 11/2017 |
| CN | 107344908 | 11/2017 |
| CN | 107382672 | 11/2017 |
| CN | 107382672 A | 11/2017 |
| CN | 107589203 | 1/2018 |
| CN | 107811904 | 3/2018 |
| CN | 107898826 | 4/2018 |
| CN | 108078965 | 5/2018 |
| CN | 207384904 | 5/2018 |
| CN | 207384906 | 5/2018 |
| CN | 108126012 | 6/2018 |
| CN | 207532828 | 6/2018 |
| CN | 108314608 | 7/2018 |
| CN | 207591325 | 7/2018 |
| CN | 108354914 | 8/2018 |
| CN | 108479098 | 9/2018 |
| CN | 207886739 | 9/2018 |
| CN | 108640820 | 10/2018 |
| CN | 108654134 | 10/2018 |
| CN | 108802240 | 11/2018 |
| CN | 108929201 | 12/2018 |
| CN | 108968071 | 12/2018 |
| CN | 108998248 | 12/2018 |
| CN | 109010638 | 12/2018 |
| CN | 109053388 | 12/2018 |
| CN | 208292897 | 12/2018 |
| CN | 109200046 | 1/2019 |
| CN | 109232191 | 1/2019 |
| CN | 109363026 | 2/2019 |
| CN | 109369344 | 2/2019 |
| CN | 208500803 | 2/2019 |
| CN | 109394836 | 3/2019 |
| CN | 109419665 | 3/2019 |
| CN | 109419851 | 3/2019 |
| CN | 109475512 | 3/2019 |
| CN | 109475586 | 3/2019 |
| CN | 109498606 | 3/2019 |
| CN | 109528583 | 3/2019 |
| CN | 109568389 | 4/2019 |
| CN | 109574810 | 4/2019 |
| CN | 109593651 | 4/2019 |
| EA | 3429580 | 1/2019 |
| EP | 494665 | 7/1992 |
| EP | 1076653 | 2/2001 |
| EP | 1633733 | 3/2006 |
| EP | 1644349 | 4/2006 |
| EP | 1803717 | 7/2007 |
| EP | 1893191 | 3/2008 |
| EP | 1896389 | 3/2008 |
| EP | 2007376 | 12/2008 |
| EP | 2037901 | 3/2009 |
| EP | 2044935 | 4/2009 |
| EP | 2146731 | 1/2010 |
| EP | 2332533 | 6/2011 |
| EP | 2444081 | 4/2012 |
| EP | 2968259 | 1/2016 |
| EP | 3028697 | 6/2016 |
| EP | 3041815 | 7/2016 |
| EP | 3067058 | 9/2016 |
| EP | 3119391 | 1/2017 |
| EP | 3206679 | 8/2017 |
| EP | 3247402 | 11/2017 |
| EP | 3253727 | 12/2017 |
| EP | 3274321 | 1/2018 |
| EP | 3310390 | 4/2018 |
| EP | 3439759 | 2/2019 |
| EP | 3442515 | 2/2019 |
| EP | 3442552 | 2/2019 |
| EP | 3445838 | 2/2019 |
| EP | 3446697 | 2/2019 |
| EP | 3449914 | 3/2019 |
| EP | 3449915 | 3/2019 |
| EP | 3449916 | 3/2019 |
| EP | 3452025 | 3/2019 |
| EP | 3452026 | 3/2019 |
| EP | 3452195 | 3/2019 |
| EP | 3454849 | 3/2019 |
| EP | 3455213 | 3/2019 |
| EP | 3463335 | 4/2019 |
| EP | 3471745 | 4/2019 |
| EP | 3471746 | 4/2019 |
| EP | 3472142 | 4/2019 |
| FR | 2966698 | 5/2012 |
| FR | 3062303 | 8/2018 |
| GB | 1481048 | 7/1977 |
| GB | 2381450 | 5/2006 |
| GB | 2393182 | 3/2007 |
| GB | 2432312 | 5/2007 |
| GB | 2450974 | 2/2012 |
| GB | 2494461 | 3/2013 |
| GB | 2492487 | 9/2015 |
| GB | 2527599 | 12/2015 |
| GB | 2495841 | 2/2016 |
| GB | 2531282 | 4/2016 |
| GB | 2542797 | 4/2017 |
| GB | 2557921 | 7/2018 |
| GB | 2560019 | 8/2018 |
| GB | 2487183 | 10/2018 |
| GB | 2530001 | 1/2019 |
| GB | 2564383 | 1/2019 |
| IN | 200502571 | 5/2007 |
| IN | 253746 B | 8/2007 |
| IN | 264549 B | 8/2007 |
| IN | 200704456 | 8/2007 |
| IN | 222132 B | 7/2008 |
| IN | 200900654 | 5/2009 |
| IN | 200907295 | 6/2010 |
| IN | 242112 B | 8/2010 |
| IN | 201409507 | 7/2015 |
| IN | 201507784 | 1/2016 |
| IN | 201617015721 A | 8/2016 |
| IN | 201737002171 A | 5/2017 |
| IN | 201717008714 A | 7/2017 |
| IN | 201727014697 A | 7/2017 |
| IN | 201737030087 A | 10/2017 |
| IN | 201504124 I3 | 11/2017 |
| IN | 201737039585 A | 12/2017 |
| IN | 201727039031 A | 4/2018 |
| IN | 81 7041 962 A | 12/2018 |
| IN | 201817042032 A | 12/2018 |
| IN | 201817039498 A | 2/2019 |
| JP | 04969767 | 1/2005 |
| JP | 06239976 | 11/2017 |
| JP | 06280489 | 2/2018 |
| KR | 141524 | 6/1998 |
| KR | 711951 | 5/2007 |
| KR | 1029306 | 4/2011 |
| KR | 2019033590 | 3/2019 |
| KR | 2019034576 | 4/2019 |
| KR | 2019035791 | 4/2019 |
| MA | 37112 | 8/2016 |
| MX | 2017005277 | 1/2018 |
| MX | 2017015647 | 8/2018 |
| RU | 2016129536 | 1/2018 |
| WO | 2005061480 | 7/2005 |
| WO | 2005120478 | 12/2005 |
| WO | 2006063109 | 6/2006 |
| WO | 2006133941 | 12/2006 |
| WO | 2007/144628 | 12/2007 |

(56) References Cited

FOREIGN PATENT DOCUMENTS

| | | |
|---|---|---|
| WO | 2008/013963 | 1/2008 |
| WO | 2009013506 | 1/2009 |
| WO | 2011/006099 | 1/2011 |
| WO | 2012160358 | 11/2012 |
| WO | 2013006953 | 1/2013 |
| WO | 2014108899 | 7/2014 |
| WO | 2015032519 | 3/2015 |
| WO | 2015122484 | 8/2015 |
| WO | 2015/191728 | 12/2015 |
| WO | 2016/004410 | 1/2016 |
| WO | 2016/092376 | 6/2016 |
| WO | 2016094810 | 6/2016 |
| WO | 2016116628 | 7/2016 |
| WO | 2016/127111 | 8/2016 |
| WO | 2016/138505 | 9/2016 |
| WO | 2016/147186 | 9/2016 |
| WO | 2016/153347 | 9/2016 |
| WO | 2016/154032 | 9/2016 |
| WO | 2016/161420 | 10/2016 |
| WO | 2016160542 | 10/2016 |
| WO | 2016/179581 | 11/2016 |
| WO | 2016/187679 | 12/2016 |
| WO | 2016/189384 | 12/2016 |
| WO | 2016205923 | 12/2016 |
| WO | 2017/011210 | 1/2017 |
| WO | 2017/051398 | 3/2017 |
| WO | 2017048750 | 3/2017 |
| WO | 2017139496 | 8/2017 |
| WO | 2017175064 | 10/2017 |
| WO | 2018048952 | 3/2018 |
| WO | 2018061007 | 4/2018 |
| WO | 2018061009 | 4/2018 |
| WO | 2018064654 | 4/2018 |
| WO | 2018065479 | 4/2018 |
| WO | 2018071372 | 4/2018 |
| WO | 2018071452 | 4/2018 |
| WO | 2018083695 | 5/2018 |
| WO | 2018089863 | 5/2018 |
| WO | 2018102711 | 6/2018 |
| WO | 2018106973 | 6/2018 |
| WO | 2018112329 | 6/2018 |
| WO | 2018113888 | 6/2018 |
| WO | 2018125857 | 7/2018 |
| WO | 2018130682 | 7/2018 |
| WO | 2018142403 | 8/2018 |
| WO | 2018152637 | 8/2018 |
| WO | 2018160510 | 9/2018 |
| WO | 2018163187 | 9/2018 |
| WO | 2018167038 | 9/2018 |
| WO | 2018170596 | 9/2018 |
| WO | 2018175796 | 9/2018 |
| WO | 2018183115 | 10/2018 |
| WO | 2018187500 | 10/2018 |
| WO | 2018195562 | 10/2018 |
| WO | 2018200888 | 11/2018 |
| WO | 2018204326 | 11/2018 |
| WO | 2018204859 | 11/2018 |
| WO | 2018205038 | 11/2018 |
| WO | 2018209425 | 11/2018 |
| WO | 2018211388 | 11/2018 |
| WO | 2018215520 | 11/2018 |
| WO | 2018222923 | 12/2018 |
| WO | 2018233991 | 12/2018 |
| WO | 2018234301 | 12/2018 |
| WO | 2018235079 | 12/2018 |
| WO | 2019002933 | 1/2019 |
| WO | 2019003226 | 1/2019 |
| WO | 2019011664 | 1/2019 |
| WO | 2019012267 | 1/2019 |
| WO | 2019014490 | 1/2019 |
| WO | 2019020738 | 1/2019 |
| WO | 2019023668 | 1/2019 |
| WO | 2019023751 | 2/2019 |
| WO | 2019023803 | 2/2019 |
| WO | 2019030561 | 2/2019 |
| WO | 2019032150 | 2/2019 |
| WO | 2019032609 | 2/2019 |
| WO | 2019034936 | 2/2019 |
| WO | 2019043259 | 3/2019 |
| WO | 2019045994 | 3/2019 |
| WO | 2019046806 | 3/2019 |
| WO | 2019049142 | 3/2019 |
| WO | 2019051560 | 3/2019 |
| WO | 2019052830 | 3/2019 |
| WO | 2019057994 | 3/2019 |
| WO | 2019063848 | 4/2019 |
| WO | 2019064031 | 4/2019 |
| WO | 2019069309 | 4/2019 |
| WO | 2019070885 | 4/2019 |
| WO | 2019071000 | 4/2019 |
| WO | 2019071302 | 4/2019 |
| WO | 2019079208 | 4/2019 |
| WO | 2019/135225 | 7/2019 |
| WO | 2020/024011 | 2/2020 |

OTHER PUBLICATIONS

PCT International Search Report and Written Opinion in International Application PCT/US2019/026093, dated Jul. 26, 2019, 10 pages.

Repetto, M., et al., "Separation of cannabinoids", 1976, United Nations Office on Drugs and Crime—Bulletin on Narcotics, issue 4-007, 5 pages (Year: 1976). (with Eng. ab.).

Straight, R., et al., "Marihuana extraction and purification for oral administration of known amounts of delta9-tetrahydrocannabinol (THC)", 1973, Biochemical Medicine, No. 8, pp. 341-344 (Year: 1973).

PCT International Search Report and Written Opinion in International Application PCT/US2019/055733, dated Feb. 5, 2020, 10 pages.

Carreras, J., et al., "Synthesis of (−)-Cannabimovone and Structural Reassignment of Anhydrocannabimovone through Gold (I)-Catalyzed Cycloisomerization", Angew Chem. Int. Ed., 2016, vol. 55, pp. 7121-7125.

PCT International Search Report and Written Opinion in International Application PCT/US2019/050094, dated Dec. 30, 2019, 9 pages.

Gunzinger, PJ et al., "Synthesis of a New Depsidone, Derivative of Furfuric Acid: Methyl 3,6-dimethoxy-9-(2,4-dimethoxy-5-methoxycarbonyl-3-6-dimethylbenzyl)-1,4,6-trimethyl-11-oxo-11H-dibenzo[b,e]dioxepin[1,4]-carboxylate", Helvetica Chimica Acta, 1985, vol. 68, 1940-1947.

Schmalz, HG., et al., "On the Deprotonation of n6-1,3-Dimethoxybenzene-Cr(CO)3 Derivatives: Influence of the Reactive Conditions on the Regioselectivity", Tetrahedron, 1997, vol. 53, No. 27, pp. 9219-9232.

Novak, J. et al., "Cannabis XXIV, A New Convenient Synthesis of Cannabinol", Tetrahedron, 1982, vol. 23, No. 2, pp. 253-254.

\* cited by examiner

CONTINUED FROM FIG.4A

========================================
Area Percent Report
========================================

Sorted By        : Signal
Multiplier       : 1.0000
Dilution         : 1.0000

Do not use Multiplier & Dilution Factor with ISTDs

Signal 1: MSD1 TIC, MS File

| Peak # | RetTime [min] | Type | Width [min] | Area | Height | Area % |
|---|---|---|---|---|---|---|
| 1 | 1.276 | BB | 0.0704 | 2.79970e6 | 6.12170e5 | 54.0029 |
| 2 | 2.423 | BB | 0.0800 | 2.38466e6 | 4.66916e5 | 45.9971 |

Totals : 5.18436e6   1.07909e6

Signal 2: MSD2 TIC, MS File

| Peak # | RetTime [min] | Type | Width [min] | Area | Height | Area % |
|---|---|---|---|---|---|---|
| 1 | 0.377 | BB | 0.0566 | 3307.41406 | 975.42657 | 37.6925 |
| 2 | 1.053 | BB | 0.0666 | 5467.32178 | 1286.79211 | 62.3075 |

Totals : 8774.73584   2262.21869

FIG.4B

CONTINUED FROM FIG.5A

```
================================================
                External Standard Report
================================================
```

Sorted By            : Signal
Calib. Data Modified : Saturday, July 30, 2016 1:37:56 PM
Multiplier           : 1.0000
Dilution             : 1.6807

Do not use Multiplier & Dilution Factor with ISTDs

Signal 1: MSD1 TIC, MS File

| RetTime [min] | Type | Area | Amt/Area | Amount [%] | Grp | Name |
|---|---|---|---|---|---|---|
| 1.294 | BB | 5.04025e6 | 7.53263e-6 | 63.80893 | | CBD |
| Totals : | | | | 63.80893 | | |

← 510

Signal 2: MSD2 TIC, MS File

```
================================================
================================================
                 Calibration Curves
================================================
```

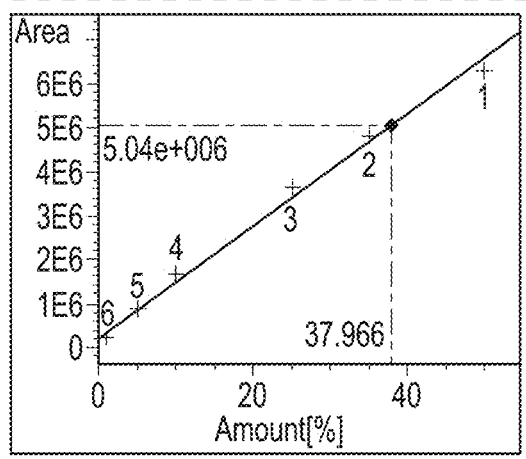

CBD at exp. RT: 1.294
MSD1 TIC, MS File
Correlation:              0.99640
Residual Std. Dev.: 226769.36090
Formula: y = mx + b
    m: 126864.69173
    b: 223664.46182
    x: Amount [%]
    y: Area

FIG.5B

CONTINUED FROM FIG.6A

============================================
External Standard Report
============================================

Sorted By         : Signal
Calib. Data Modified : Saturday, July 30, 2016 1:37:56 PM
Multiplier        : 1.0000
Dilution          : 1.8904

Do not use Multiplier & Dilution Factor with ISTDs

Signal 1: MSD1 TIC, MS File

| RetTime [min] | Type | Area | Amt/Area | Amount [%] | Grp | Name |
|---|---|---|---|---|---|---|
| 1.295 | BB | 4.60626e6 | 7.49967e-6 | 65.30328 | | CBD |

Totals :                                    65.30328 — 610

Signal 2: MSD2 TIC, MS File

============================================
Calibration Curves
============================================

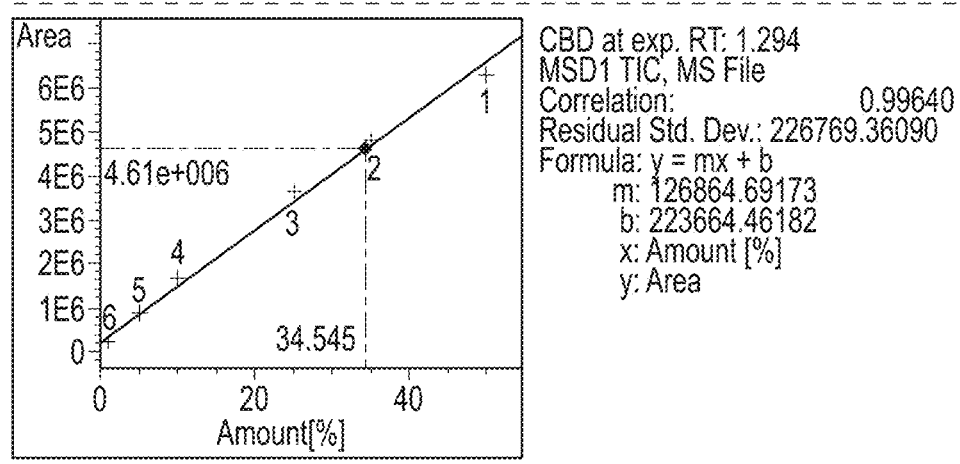

FIG.6B

CONTINUED FROM FIG.7A

===================================
External Standard Report
===================================

Sorted By            : Signal
Calib. Data Modified : Saturday, July 30, 2016 1:37:56 PM
Multiplier           : 1.0000
Dilution             : 1.8116
Do not use Multiplier & Dilution Factor with ISTDs Signal 1: MSD1 TIC, MS File

```
RetTime  Type   Area        Amt/Area     Amount    Grp  Name
 [min]                                   [%]
--------|-----|-----------|------------|----------|---|-----------
  1.296  BB    5.04772e6   7.53314e-6   68.88617       CBD
Totals :                                68.88617              710
```
Signal 2: MSD2 TIC, MS File ===================================
===================================
Calibration Curves
===================================

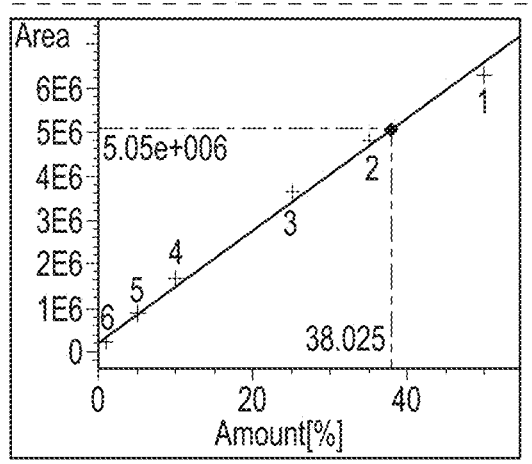

CBD at exp. RT: 1.294
MSD1 TIC, MS File
Correlation:              0.99640
Residual Std. Dev.: 226769.36090
Formula: y = mx + b
    m: 126864.69173
    b: 223664.46182
    x: Amount [%]
    y: Area

FIG.7B

CONTINUED FROM FIG.8A

═══════════════════════════════════════
External Standard Report
═══════════════════════════════════════

Sorted By           : Signal
Calib. Data Modified : Saturday, July 30, 2016 1:37:56 PM
Multiplier          : 1.0000
Dilution            : 1.8904

Do not use Multiplier & Dilution Factor with ISTDs

Signal 1: MSD1 TIC, MS File

| RetTime [min] | Type | Area | Amt/Area | Amount [%] | Grp | Name |
|---|---|---|---|---|---|---|
| 1.296 | BB | 4.89610e6 | 7.52233e-6 | 69.62212 | | CBD — 810 |
| Totals : | | | | 69.62212 | | |

Signal 2: MSD2 TIC, MS File

═══════════════════════════════════════
Calibration Curves
═══════════════════════════════════════

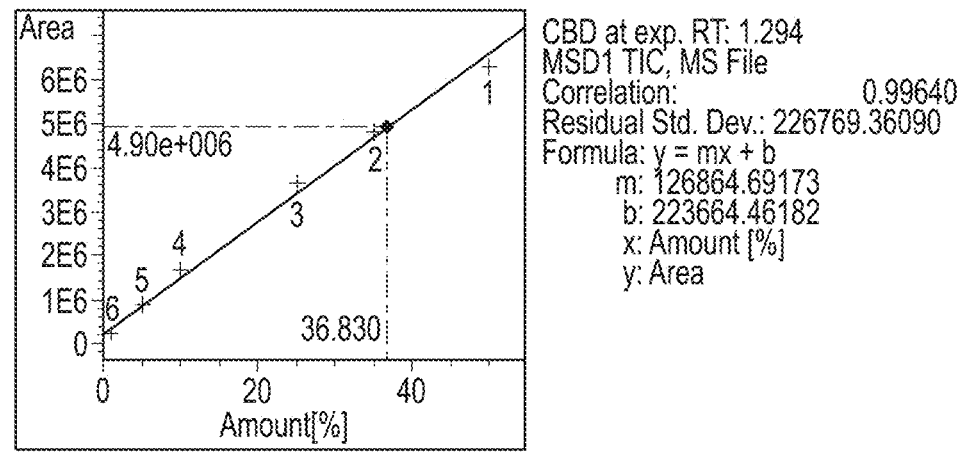

FIG.8B

CONTINUED FROM FIG.9A

========================================
External Standard Report
========================================

Sorted By                : Signal
Calib. Data Modified     : Saturday, July 30, 2016 1:37:56 PM
Multiplier               : 1.0000
Dilution                 : 2.0956

Do not use Multiplier & Dilution Factor with ISTDs

Signal 1: MSD1 TIC, MS File

| RetTime [min] | Type | Area | Amt/Area | Amount [%] | Grp | Name |
|---|---|---|---|---|---|---|
| 1.296 | BB | 5.98284e6 | 7.58774e-6 | 95.13038 | | CBD |
| Totals : | | | | 95.13038 | | |

— 910

Signal 2: MSD2 TIC, MS File

========================================
Calibration Curves
========================================

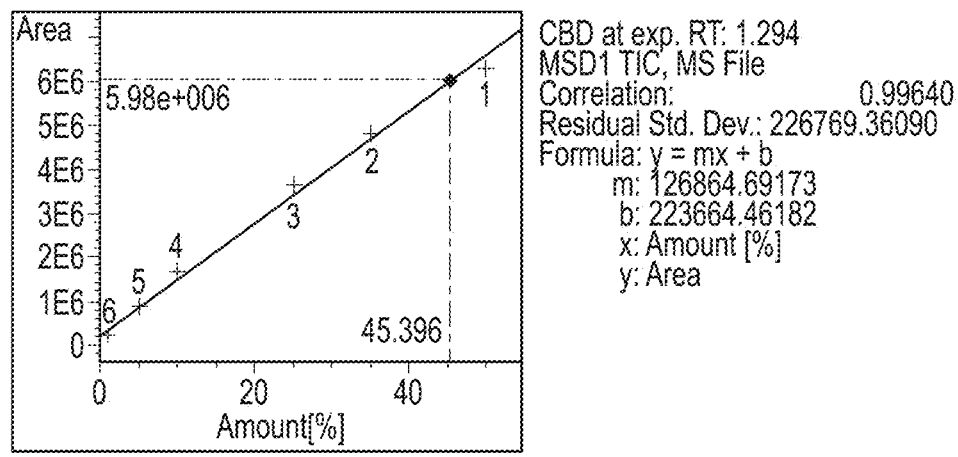

FIG.9B

CANNABIS EXTRACTS

CROSS-REFERENCE TO RELATED APPLICATIONS

This application is a continuation application and claims priority to U.S. patent application Ser. No. 15/834,826, filed Dec. 7, 2017, U.S. Pat. No. 10,239,808, which claims priority to U.S. Provisional Application No. 62/431,209, filed Dec. 7, 2016, which are incorporated by reference herein in their entirety.

BACKGROUND

Cannabis plant material contains a variety of potentially valuable compounds. For example tetrahydrocannabinol (THC), cannabidiol (CBD), cannabichromene (CBC), cannabigerol (CBG), cannabinol (CBN), and other compounds are present in varying amounts in cannabis and hemp plant material.

As defined by Congress, in order for a cannabis plant to qualify as industrial hemp, the THC content must be below 0.3% of overall mass. However, current extraction processes typically increase THC content of industrial hemp based oil to an average of 3.5% of overall mass. This product is now legally defined by Congress as "marihuana" and is no longer regulatory compliant. The most widely employed solution to this problem is the dilution of product through a myriad of unknown additives, which not only decreases the THC content, but in decrease turn all medical cannabinoids by 10 fold. Alternatively CBD isolates are a popular solution, though these concentrates inevitably render the terpenes, fatty acids, and full spectrum cannabinoid profile unusable. In another attempt to solve the problem, fractional distillation is being explored; however, distillation would be very difficult to make as a viable solution on a commercial scale, due to costs associated with industrial refineries and the similar boiling points of cannabinoids, the need to still add dilutant and the excessive product loss associated with the process.

Thus, efficient methods are desirable for processing cannabis oil to provide a clean cannabis oil comprising not more than 0.3 wt % THC compared to overall mass, while otherwise maintaining cannabinoid profile, including other cannabinoids, terpenes and fatty acids.

Raw cannabis oil containing these and other compounds may be extracted from the cannabis flower/plant using techniques such as $CO_2$ extraction or liquid-solid solvent extraction. The concentration of compounds in the raw cannabis oil, however, is currently not well controlled. Typical control techniques include diluting the cannabis oil with a foreign substance, such as olive oil, MCT oil, and hempseed oil. This technique does not change the relative concentrations of the compounds vis-à-vis other compounds in the cannabis oil. Other techniques target the removal of specific compounds, such as THC. This, however, often results in other compounds being removed or denatured as a result. Thus, it remains desirous to identify methods to separate raw cannabis oil into one or more of its constituent compounds.

It is with respect to these and other considerations that the technology is disclosed. Also, although relatively specific problems have been discussed, it should be understood that the embodiments presented should not be limited to solving the specific problems identified in the introduction.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

The technology described herein includes systems and methods to extract various compounds from raw cannabis oil. A liquid chromatography system may be used to extract specific compounds from raw cannabis oil.

In an embodiment, the technology relates to a method for extracting compounds from raw cannabis oil.

In some embodiments, a preparatory method is provided for removing one or more cannabis compounds from a cannabis oil, the method comprising: obtaining a column packed with a stationary phase particulate; adding cannabis oil to the packed column; adding a first eluent to the packed column; adding a second eluent to the packed column; collecting at least two eluate fractions comprising one or more compounds; disposing of at least one of the at least two eluate fractions; and evaporating at least one of the remaining at least two fractions to form a composition. In some embodiments, the method comprises adding a third eluent is to the packed column.

In embodiments, the stationary phase particulate is selected from normal phase or reverse phase stationary phase. In a specific embodiment, the column is a normal phase silica gel stationary phase column. In other embodiments, a reverse phase stationary phase is selected from the group consisting of C18, C8, C4 and phenyl stationary phase particulate.

In some embodiments, a normal phase column is employed, and a mobile phase comprising a first eluent and second eluent are used to elute the column. In some embodiments, the first eluent and second eluent are different and each is selected from one or more of petroleum ether, pentane, n-hexane, hexanes, diethyl ether, ethyl acetate, and ethanol. In some embodiments, the first eluent and the second eluent are each solvents selected from one or, or a specific mixture of two or more of, the group consisting of petroleum ether, pentane, n-hexane, hexanes, diethyl ether, ethyl acetate, and ethanol. In some embodiments, the first eluent and second eluent are each solvents selected from one of, or a specific mixture of two or more of, the group consisting of petroleum ether, pentane, n-hexane, hexanes, n-heptane, heptanes, diethyl ether, methyl tert butyl ether, ethyl acetate, and ethanol.

In embodiments, the first eluent and the second eluent are each solvents selected from one of, or a specific mixture of two or more of, the group consisting of petroleum ether, n-hexane, hexanes, n-heptane, heptanes, diethyl ether, and methyl tert butyl ether. In embodiments, the first eluent and the second eluent are each a mixture of diethyl ether and petroleum ether. In embodiments, the first eluent and the second eluent are each a mixture of methyl tert butyl ether and petroleum ether. In embodiments, the first eluent and the second eluent are each a mixture of diethyl ether and n-heptane or a heptane. In embodiments, the first eluent and the second eluent are each a mixture of methyl tert butyl ether and n-heptane or a heptane.

In some embodiments, the normal phase column is eluted with a first eluent solvent system selected from 90-97 vol % petroleum ether with 3-10 vol % of a mixture of from 90-100 vol % diethyl ether with 0-10 vol % ethanol; 90-97 vol % pentane with 3-10 vol % of a mixture of from 90-100 vol % diethyl ether with 0-10 vol % ethanol; 90-97 vol % n-hexane with 3-10% of a mixture of from 90-100 vol % diethyl ether with 0-10 vol % ethanol.

In some specific embodiments, the normal phase column is eluted with a first eluent solvent system selected from 92 vol % petroleum ether and 8 vol % of a mixture of 95% diethyl ether/5% ethanol; 92 vol % pentane and 8 vol % of a mixture of 95% diethyl ether/5% ethanol; 92 vol % n-hexane and 8 vol % of a mixture of 95% diethyl ether/5% ethanol; 96 vol % petroleum ether and 4 vol % of a mixture of 95% diethyl ether/5% ethanol; 96 vol % pentane and 4 vol % of a mixture of 95% diethyl ether/5% ethanol; or 96 vol % n-hexane and 4 vol % of a mixture of 95% diethyl ether/5% ethanol.

In some embodiments, the normal phase column is eluted with a second eluent solvent system selected from: 60-80 vol % petroleum ether with 20-40 vol % of a mixture of from 90-100 vol % diethyl ether/0-10 vol % ethanol; 60-80 vol % pentane with 20-40 vol % of a mixture of a mixture of from 90-100 vol % diethyl ether/0-10 vol % ethanol; or 60-80 vol % n-hexane with 20-40 vol % of a mixture of from 90-100 vol % diethyl ether/0-10 vol % ethanol.

In some specific embodiments, the normal phase column is eluted with a second eluent solvent system selected from: 70 vol % petroleum ether and 30% of a mixture of 95% diethyl ether/5% ethanol; 70 vol % pentane and 30 vol % of a mixture of 95% diethyl ether/5% ethanol; 70 vol % n-hexane and 30 vol % of a mixture of 95% diethyl ether/5% ethanol; 60 vol % petroleum ether and 40 vol % of a mixture of 95% diethyl ether/5% ethanol; 60 vol % pentane and 40 vol % of a mixture of 95% diethyl ether/5% ethanol; or 60 vol % n-hexane and 40 vol % of a mixture of 95% diethyl ether/5% ethanol.

In embodiments, the second eluent is selected from 30-40 vol % water with 0.05-1 vol % formic acid and 70-60 vol % ethanol with 0.05-1 vol % formic acid; or 30-40 vol % water with 0.05-1 vol % formic acid and 70-60 vol % acetonitrile with 0.05-1 vol % formic acid.

In embodiments, the second eluent is selected from 20-30 vol % water with 0.05-1 vol % formic acid and 70-80 vol % ethanol with 0.05-1 vol % formic acid; or 20-30 vol % water with 0.05-1 vol % formic acid and 70-80 vol % acetonitrile with 0.05-1 vol % formic acid.

In some specific embodiments, the normal phase column is eluted with a first eluent in a volume of between one and eleven column volumes (CVs), 2 to 7 CVs, or 4 to 6 CVs; and a second eluent in a volume of between one and eleven column volumes (CVs), 2 to 7 CVs, or 4 to 6 CVs.

In some embodiments, a reverse phase column is employed and a mobile phase comprising a first eluent and second eluent are used to elute the column. In some embodiments, the first eluent and second eluent are different and each is selected from one or more of water, acetonitrile, and ethanol, with or without an acidic modifier. In some embodiments, the reverse phase stationary phase column is eluted with a first eluent selected from 30-40 vol % water and 70-60 vol % ethanol optionally containing an organic acid modifier selected from formic acid or trifluoroacetic acid in from 0.01-0.2 vol %; or 30-40 vol % water and 70-60 vol % acetonitrile; wherein the first eluent optionally containing an organic acid modifier selected from formic acid or trifluoroacetic acid in from 0.01-0.2 vol %.

In some specific embodiments, the reverse phase column is eluted with a second eluent selected from 20-30 vol % water and 70-80 vol % ethanol; or 20-30 vol % water and 70-80 vol % acetonitrile, optionally wherein the first and second eluent contain an organic acid modifier selected from formic acid or trifluoroacetic acid in from 0.01-0.2 vol %.

In one embodiment, the method comprises pooling the normal phase eluate from 6-7.5 column volumes, evaporating the pooled eluate to form a composition, and recrystallizing the composition to provide a purified composition comprising cannabidiol (CBD) in greater than 94% purity, having not more than 0.3% THC. In embodiments, the purified composition comprises CBD after recrystallization having at least 94% purity. In embodiments, the purified composition comprises CBD after recrystallization having at least 95% purity. In embodiments, the purified composition comprises CBD after recrystallization having at least 96% purity. In embodiments, the purified composition comprises CBD after recrystallization having at least 97% purity. In embodiments, the purified composition comprises CBD after recrystallization having at least 98% purity. In embodiments, the purified composition comprises CBD after recrystallization having at least 99% purity. In embodiments, the purified composition comprises CBD after recrystallization having 100% purity. In embodiments, after evaporation and prior to recrystallization the composition comprises CBD having a purity of 90-95%. In some embodiments, the CBD is recrystallized from pentane, n-hexane, petroleum ether, or a mixture thereof.

In some embodiments, the method comprises pooling the normal phase eluate from 1-6 and 9-12 CVs, and evaporating to provide a composition comprising 60-75% CBD, 0.001-0.5% THC, 0.1-8% CBC, CBG, CBN, and about 5-25% fatty acids and terpenes. In some embodiments, the composition comprises 65-70% CBD, not more than 0.3% THC, 0.3-5% CBC, 0.3-5% CBG, 0.3-5% CBN, and about 10-20% fatty acids and terpenes. In some embodiments, the composition comprises 65-70% CBD, not more than 0.2% THC, 0.3-5% CBC, and about 15% fatty acids and terpenes.

In another embodiment, a method is provided for processing raw cannabis oil to provide clean cannabis oil, or a CBD isolate, having less than 0.3 wt % delta-9-THC, the method comprising: obtaining raw cannabis oil; applying the raw cannabis oil to a normal stationary phase column; eluting the normal stationary phase column with a binary solvent system wherein the binary solvent system comprises a first solvent A and a second solvent B; fractionating the eluate into at least two eluate fractions; disposing at least one of the at least two eluate fractions; and evaporating the solvent from the remaining at least two eluate fractions to provide the clean cannabis oil comprising less than 0.3 wt % THC. In a specific embodiment, the normal stationary phase column is a silica gel column.

In some embodiments, the raw cannabis oil is obtained by supercritical $CO_2$ extraction of Cannabis spp. plant material, solvent-solid extraction of Cannabis spp. plant material, or from a commercial supplier.

In some embodiments, the first solvent A in the binary solvent system is a non-polar solvent selected from one or more of the group consisting of pentane, petroleum ether, hexanes, n-hexane, heptane, diisopropyl ether, toluene, chloroform, and methylene chloride; preferably petroleum ether, hexanes, or n-hexane. In embodiments, the first solvent A in the binary solvent system is a non-polar solvent selected from one or more of the group consisting of pentane, petroleum ether, hexanes, n-hexane, n-heptane, heptanes, diisopropyl ether, toluene, chloroform, and methylene chloride. In embodiments, the first solvent A in the binary solvent system is petroleum ether, a heptane, or n-heptane.

In some embodiments, the second solvent B in the binary solvent system is a polar solvent selected from one or more of the group consisting of diethyl ether, tetrahydrofuran, ethyl acetate, acetone, acetonitrile, isopropanol, ethanol, and methanol; preferably diethyl ether, a mixture of diethyl ether and ethanol, or ethyl acetate. In embodiments, the second solvent B in the binary solvent system is a polar solvent selected from one or more of the group consisting of diethyl ether, methyl tert butyl ether, tetrahydrofuran, ethyl acetate, acetone, acetonitrile, isopropanol, ethanol, and methanol. In embodiments, the polar solvent is diethyl ether or methyl tert butyl ether.

In some embodiments, the normal phase column is eluted with a step gradient using a binary solvent system comprising the first solvent A and the second solvent B, wherein solvent A is petroleum ether, pentane, or n-hexane and the solvent B is a mixture of 90-100:0-10 v/v diethyl ether/ethanol. In a specific embodiment, the column is eluted with a mixture of solvent A/solvent B at 8% solvent B for 7 CV, then 30% solvent B for 6 CV. In embodiments, the column is eluted with a step gradient using a binary solvent system comprising the first solvent A and the second solvent B, wherein solvent A is petroleum ether, a heptane, or n-heptane and solvent B is diethyl ether or methyl tert butyl ether.

In some embodiments, the normal phase column is eluted and eluate from 0-6 column volumes and 9-12.5 column volumes are pooled, and concentrated to provide clean cannabis oil having not more than 0.3 wt % THC and about 60-70 wt % CBD.

In specific embodiments, the yield of clean cannabis oil is not less than 60 wt %, or not less than 65 wt % based on starting raw cannabis oil.

In embodiments, the solvent A is petroleum ether, solvent B is 95% diethyl ether and 5% ethanol, and the eluate fractions from 0-6 column volumes and 9-12 column volumes are pooled, and concentrated to provide clean cannabis oil having not more than 0.3 wt % THC and about 60-70 wt % CBD.

In embodiments, applying comprises loading 1 to 20 wt %, 2 to 15 wt %, or 4 to 8 wt % of the raw cannabis oil to the normal stationary phase column, when compared to the total weight of the normal stationary phase.

In a specific embodiment, the disclosure provides a composition comprising about 65-70% CBD, not more than 0.3% THC, 0.3-5% CBC, 0.3-5% CBG, 0.3-5% CBN, and about 10-20% fatty acids and terpenes. Also disclosed herein is a composition comprising about 40-80% CBD, not more than 0.3% THC, 0.3-5% CBC, 0.3-5% CBG, and 0.3-5% CBN.

Also disclosed herein are processes that can concentrate cannabidiol (CBD) from a cannabis oil prior to performing the chromatography methods disclosed herein. A method of concentrating CBD from a cannabis oil disclosed herein comprises: mixing petroleum ether with a heated cannabis oil to provide a mixture; allowing the mixture to cool to room temperature; cooling the mixture to 0° C. to provide a cooled mixture; mixing a first amount of petroleum ether at −10° C. to 0° C. into the cooled mixture; freezing the cooled mixture for at least two hours or cooling the cooled mixture at 0° C.; adding a second amount of petroleum ether at −10° C. to 0° C. to the mixture; filtering the mixture to provide a filtrate and a concentrate; and collecting the concentrate, wherein the concentrate comprises CBD having at least about 94% purity and the concentrate has not more than 0.3% THC. In embodiments, the concentrate comprises CBD having 90-95% purity.

In embodiments, the cooled mixture is frozen for 2-24 hours or 6-24 hours, for example, for 2-18 hours or for 6-18 hours.

In embodiments, the concentrate does not include THC. In embodiments, the concentrate does not include CBG. In embodiments, the concentrate does not include CBC. In embodiments, the concentrate does not include CBN. As used herein, in embodiments, "does not include" means that the component is below a detectable limit.

In embodiments, the method further comprises performing a recrystallization of the concentrate after collecting the concentrate, wherein the recrystallization provides CBD having greater than 95% purity. In embodiments, the recrystallization provides CBD having at least 98% purity. In embodiments, the recrystallization provides CBD having at least 99% purity. In embodiments, the recrystallization provides CBD having at least 99.5% purity. In embodiments, the recrystallization provides CBD having 100% purity. The recrystallization can involve one or more recrystallization steps. In embodiments, the recrystallization in a single recrystallization. In embodiments, the recrystallization is two recrystallizations.

In embodiments, filting the mixture comprises filtering the mixture both at atmospheric pressure and under vacuum.

In embodiments, the method further comprises collecting the filtrate, wherein the filtrate contains CBD in an amount from about 20 wt % to about 70 wt % less than CBD present in the cannabis oil. For example, the filtrate can contain CBD in an amount from about 20 wt % to about 50 wt %, from about 40 wt % to about 60 wt %, or from about 45 wt % to about 60 wt %.

Further disclosed herein are processes that take a cannabinoids fraction arising from the chromatography methods disclosed herein and provide CBG, CBC, or a mixture thereof from the cannabinoids fraction.

According to a method, a cannabinoids fraction (e.g., provided as a product of the chromatography methods disclosed herein) is subjected to mixing ethanol at 50-70° C. into the cannabinoids fraction to provide a mixture; performing reverse phase chromatography on the mixture providing multiple CVs; identifying CVs containing CBG; concentrating the CVs containing CBG; and recrystallizing CBG, wherein the CBG has a purity of at least 94%. In embodiments, the CBG is a hydrate of CBG having 100% purity. In embodiments, the CBG is a monohydrate of CBG having 100% purity. In embodiments, the CBG is not recrystallized. In these embodiments, concentrating the CVs containing CBG provides an oil containing CBG having a purity of at least 90%.

According to a method, a cannabinoids fraction (e.g., provided as a product of the chromatography methods disclosed herein) is subjected to mixing ethanol at 50-70° C. into the cannabinoids fraction to provide a mixture; performing reverse phase chromatography on the mixture providing multiple CVs; identifying CVs containing CBC; and concentrating the CVs containing CBC to provide a CBC oil. In embodiments, the CBC oil has a purity from 94%-96%. In embodiments, the CBC oil has a purity from 90-96%.

When the CBG is not recrystallized, the oil containing CBG and the oil containing CBC can be recombined to provide a mixture comprising CBC and CBG.

According to a method, a cannabinioids fraction (e.g., provided as a product of the chromatography methods disclosed herein) is subjected to mixing ethanol at 50-70° C. into the cannabinoids fraction to provide a mixture; performing reverse phase chromatography on the mixture providing multiple CVs; identifying CVs containing CBG and CBC; and concentrating the CVs containing CBG and CBC to provide an oil comprising CBG and CBC, wherein the CBG has a purity of at least 90%. In embodiments, the oil comprises CBC having a purity from 94-96%. In embodiments, the oil comprises CBC having a purity from 90-96%.

In embodiments, the CVs containing CBG are identified by thin layer chromatography. In embodiments, the CVs containing CBC are identified by thin layer chromatography. In embodiments, the CVs containing CBG and CBC are identified by thin layer chromatography.

In embodiments, performing reverse phase chromatography comprises: eluting a column with a first solvent for 3 CV; eluting the column with the first solvent for 4 CV; and eluting the column with a second solvent for 7 CV, wherein fractions collected from 2 CV to 3.5 CV contain CBG.

In embodiments, performing reverse phase chromatography comprises eluting a column with a first solvent for 3 CV; eluting the column with the first solvent for 4 CV; and eluting the column with a second solvent for 7 CV, wherein fractions collected from 6-9 CV contain CBC.

In embodiments, the first solvent is 80% methanol and 20% distilled water and the second solvent is 85% methanol and 15% distilled water.

In embodiments, performing reverse phase chromatography comprises eluting a column with a step gradient using a binary solvent system comprising a first solvent A and a second solvent B, wherein the solvent A is methanol, ethanol, or acetonitrile and the second solvent B is distilled water. In embodiments, the first solvent A is methanol and the second solvent B is distilled water.

Also disclosed herein is an oil containing CBG produced by these methods. Further disclosed herein is an oil containing CBC produced by these methods.

Additionally disclosed herein is a mixture comprising CBG and the CBC produced by these methods having less than 0.3% THC. In embodiments, the mixture comprising CBG and CBC does not include THC. Again, as used herein, in embodiments, "does not include" means that the component is below a detectable limit. The mixture can have a CBG content and a CBC content that is approximately equal. The mixture can have 50 wt % CBG and 50 wt % CBC.

Further disclosed herein is a hydrate of CBG. Additionally, disclosed herein is a monohydrate of CBG.

BRIEF DESCRIPTION OF THE DRAWINGS

FIGS. 4A and 4B illustrate analytical HPLC-MS chromatograms a combined standard of CBD and THC.

FIGS. 5A and 5B illustrate analytical HPLC-MS chromatograms of crude oil.

FIGS. 6A and 6B illustrate analytical HPLC-MS chromatograms of diluted raw cannabis oil.

FIGS. 7A and 7B illustrate analytical HPLC-MS chromatograms for a combined fraction extracted from sample cannabis oil.

FIGS. 8A and 8B illustrate analytical HPLC-MS chromatogram for a combined and diluted sample cannabis oil.

FIGS. 9A and 9B illustrate analytical HPLC-MS chromatogram for isolate A.

DETAILED DESCRIPTION

Definitions

Figure 1:
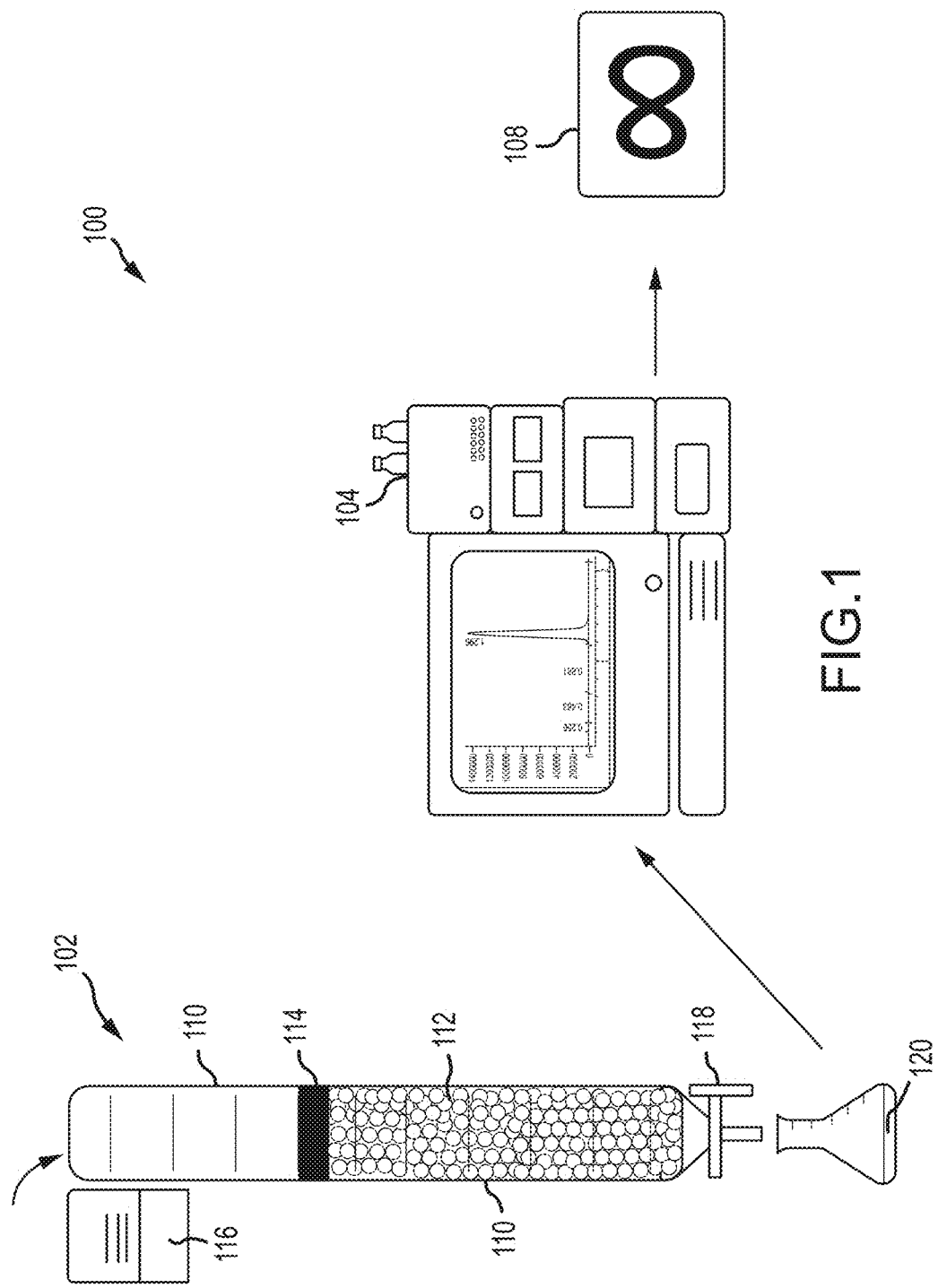
FIG. 1 illustrates a liquid chromatography system.

The terminology used in the disclosure herein is for the purpose of describing particular embodiments only and is not intended to be limiting of the disclosure. As used in the description of the embodiments of the disclosure and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

The present technology relates to extracting various compounds from bulk cannabis oil using liquid chromatography. In aspects of the technology, an extraction process, such as $CO_2$ extraction, or liquid-solid solvent extraction, is performed on cannabis plant material. In some embodiments, the resulting extract, referred to herein as raw cannabis oil or bulk cannabis oil, may contain a variety of cannabinoids and other substances. For example, tetrahydrocannabinol (THC, d9-THC, 1-trans-delta-9-tetrahydrocannabinol), cannabidiol (CBD), Cannabigerol (CBG), Cannabichromene (CBC), Cannabicyclol (CBL), Cannabinol (CBN), Cannabivarin (CBV), delta-9 Tetrahydrocannabinolic acid (THCA, d9-THCA), Tetrahydrocannabivarin (THCV), Cannabidiolic acid (CBDA), Cannabigerolic acid (CBGA), Cannabidivarin (CBDV), Cannabichromevarin (CBCV), Cannabigerovarin (CBGV), and Cannabigerol Monomethyl Ether (CBGM) may be present in varying concentrations in the raw cannabis oil.

In some embodiments, a method is provided to remove or deplete a THC component from crude cannabis oil, industrial hemp extracts, or hemp oil. Methods are provided to process crude cannabis oil, industrial hemp extract, or hemp oil, to provide a clean cannabis oil. In some embodiments, the clean cannabis oil comprises from 0.001-3 wt %, 0.01-2 wt %, or 0.1-0.3 wt % THC; or not more than 1.0 wt %, 0.5 wt %, 0.3 wt %, 0.2 wt %, 0.1 wt %, or 0.05 wt % THC. In other embodiments, a method is provided to remove or deplete THC from crude cannabis oil, or hemp oil, to provide a clean cannabis oil having a cannabinoid profile of about 40-70% CBD, 1-3% CBG, 1-3% CBC, 1-3% CBN, 1-5% CBDA, 1-5% THCA, and 10-30% fatty acids and terpenes, and not more than 3 wt %, 2 wt %, 0.8 wt %, 0.5 wt %, 0.4 wt %, 0.3 wt %, 0.2 wt %, 0.1 wt %, or 0.05 wt % THC.

In a specific embodiment, a method is provided to process crude cannabis oil, industrial hemp extracts, or hemp oil to provide a clean cannabis oil having not more than 70 wt % CBD and not more than 0.3 wt % THC. In some embodiments, the clean cannabis oil comprises 40-70 wt %, 50-70 wt %, 55-70 wt %, or 65-70 wt % CBD, and not more than 0.3 wt % THC. In a specific embodiment, the clean cannabis oil comprises 65-70% CBD, <0.3% THC, 0.3-5% CBC, 0.3-5% CBG, 0.3-5% CBN, and ~15% fatty acids and terpenes.

In some embodiments, a clean cannabis oil is provided containing from about 0.1-10 wt %, 0.5-8 wt %, 1-7 wt %, 2-6 wt %, or about 3-5 wt % terpenes comprising one or more, two or more or three or more terpenes selected from the group consisting of myrcene, linolool, limonene, beta-caryophyllene (beta-humulene), alpha-caryophyllene (alpha-humulene), alpha-pinene, beta-pinene, alpha-bisabolol, delta-3-carene, trans-gamma-bisabolene, borneol, terpineol, eucalyptol, trans-ocimene, trans-alpha-farnesene, cis-beta-farnesene, gamma-curcumene, beta-fenchol, fenchone, beta-phellandrene, guajol, alpha-guaiene, alpha-eudesmol, terpinolene, alpha-selinene, camphene, alpha-thujene, and cineole.

In some embodiments, a clean cannabis oil is provided comprising about 5-30 wt %, 6-25 wt %, 7-20 wt %, 8-15 wt %, or 9-12 wt % fatty acids, comprising both unsaturated fatty acids selected and saturated fatty acids. The clean cannabis oil may comprise one or more unsaturated fatty acids selected from linoleic acid, alpha-linolenic acid, oleic acid, gamma-linolenic acid, stearidonic acid, eicosanoic acid, cis-vaccenic acid, and isolinolenic acid. The clean cannabis oil may comprise one or more saturated fatty acids selected from palmitic acid, stearic acid, arachidonic acid, behenic acid, myristic acid, lignoceric acid, caproic acid, heptanoic acid, caprylic acid, pelargonic acid, capric acid, lauric acid, margaric acid, and isoarachidic acid.

In other embodiments, a method is provided for processing crude cannabis oil to provide a CBD isolate enriched in CBD, compared to the starting raw cannabis oil. In some embodiments, the CBD isolate comprises CBD in from 70 wt %-99.99 wt %, 75-99.9 wt %, 80-99 wt %, 90-98 wt %, or 94-98 wt %, CBD, or not less than 90 wt %, 94 wt %, 95 wt %, 97.5 wt %, 98 wt %, 99 wt %, 99.5 wt %, or not less than 99.9 wt % CBD, while comprising not more than 0.3 wt % of THC. In certain aspects, the CBD isolate contains not more than 1 wt %, 0.5 wt %, 0.3 wt % of any of THCV, THCV, CBC, CBN, CBG, THCA, CBDA, CBGA, and CBDV.

In some embodiments, the individual components are identified and/or quantified by any technique known in the art. For example, comparison to HPLC standards, HPLC, HPLC-MS, GC, GC-MS, IR, MS, $^1$H-NMR, $^{13}$C-NMR, and/or elemental analysis.

In other embodiments, because the industrial hemp market is rapidly expanding and as federal regulations on the medical study of cannabinoids relax, there will likely be an increased demand for not only CBD but a myriad of other non-psychoactive cannabinoids.

In some embodiments, methods are provided herein for processing raw cannabis oil to allow for the isolation and or depletion of individual cannabinoid and custom formulation of over ten individual medicinally relevant cannabinoids selected from one or more, two or more, three or more, four or more, five or more, six or more, seven or more, or eight or more, or nine cannabinoids selected from the group consisting of CBD, THCV, D9-THC (THC), D8-THC, CBC, CBN, CBG, THCA, CBDA, CBGA, and CBDV.

In other embodiments, a method is provided for processing crude cannabis oil to provide a THCV isolate enriched in THCV, compared to the starting raw cannabis oil. In some embodiments, the THCV isolate comprises THCV in from 70 wt %-99.99 wt %, 75-99.9 wt %, 80-99 wt %, 90-98 wt %, or 95-98 wt % THCV, or not less than 95 wt %, 97.5 wt %, 98 wt %, 99 wt %, 99.5 wt %, or not less than 99.9 wt % THCV, while comprising not more than 0.3 wt % of a cannabinoid selected from the group consisting of THC, CBD, CBC, CBN, CBG, THCA, CBDA, CBGA, and CBDV.

In other embodiments, a method is provided for processing crude cannabis oil to provide a THC isolate enriched in THC, compared to the starting raw cannabis oil. In some embodiments, the THC isolate comprises THC in from 70 wt %-99.99 wt %, 75-99.9 wt %, 80-99 wt %, 90-98 wt %, or 95-98 wt % THC, or not less than 95 wt %, 97.5 wt %, 98 wt %, 99 wt %, 99.5 wt %, or not less than 99.9 wt % THC, while comprising not more than 0.3 wt % of a cannabinoid selected from the group consisting of CBD, THCV, CBC, CBN, CBG, THCA, CBDA, CBGA, and CBDV.

In other embodiments, a method is provided for processing crude cannabis oil to provide a CBC isolate enriched in CBC, compared to the starting raw cannabis oil. In some embodiments, the CBC isolate comprises CBC in from 70 wt %-99.99 wt %, 75-99.9 wt %, 80-99 wt %, 90-98 wt %, or 95-98 wt % CBC, or not less than 95 wt %, 97.5 wt %, 98 wt %, 99 wt %, 99.5 wt %, or not less than 99.9 wt % CBC, while comprising not more than 0.3 wt % of a cannabinoid selected from the group consisting of CBD, THC, THCV, CBN, CBG, THCA, CBDA, CBGA, and CBDV.

In other embodiments, a method is provided for processing crude cannabis oil to provide a CBN isolate enriched in CBN, compared to the starting raw cannabis oil. In some embodiments, the CBN isolate comprises CBN in from 70 wt %-99.99 wt %, 75-99.9 wt %, 80-99 wt %, 90-98 wt %, or 95-98 wt % CBN, or not less than 95 wt %, 97.5 wt %, 98 wt %, 99 wt %, 99.5 wt %, or not less than 99.9 wt % CBN, while comprising not more than 0.3 wt % of a cannabinoid selected from the group consisting of THC, CBD, THCV, CBC, CBG, THCA, CBDA, CBGA, and CBDV.

In other embodiments, a method is provided for processing crude cannabis oil to provide a CBG isolate enriched in CBG, compared to the starting raw cannabis oil. In some embodiments, the CBG isolate comprises CBG in from 70 wt %-99.99 wt %, 75-99.9 wt %, 80-99 wt %, 90-98 wt %, or 95-98 wt % CBG, or not less than 95 wt %, 97.5 wt %, 98 wt %, 99 wt %, 99.5 wt %, or not less than 99.9 wt % CBD, while comprising not more than 0.3 wt % of a cannabinoid selected from the group consisting of THC, CBD, CBC, CBN, THCV, THCA, CBDA, CBGA, and CBDV.

In other embodiments, a method is provided for processing crude cannabis oil to provide a THCA isolate enriched in THCA, compared to the starting raw cannabis oil. In some embodiments, the THCA isolate comprises THCA in from 70 wt %-99.99 wt %, 75-99.9 wt %, 80-99 wt %, 90-98 wt %, or 95-98 wt % THCA, or not less than 95 wt %, 97.5 wt %, 98 wt %, 99 wt %, 99.5 wt %, or not less than 99.9 wt % THCA, while comprising not more than 0.3 wt % of a cannabinoid selected from the group consisting of THC, CBD, CBC, CBG, CBN, THCV, CBDA, CBGA, and CBDV.

In other embodiments, a method is provided for processing crude cannabis oil to provide a CBDA isolate enriched in CBDA, compared to the starting raw cannabis oil. In some embodiments, the CBDA isolate comprises CBDA in from 70 wt %-99.99 wt %, 75-99.9 wt %, 80-99 wt %, 90-98 wt %, or 95-98 wt % CBDA, or not less than 95 wt %, 97.5 wt %, 98 wt %, 99 wt %, 99.5 wt %, or not less than 99.9 wt % CBDA, while comprising not more than 0.3 wt % of a cannabinoid selected from the group consisting of THC, CBD, CBC, CBG, CBN, THCV, THCA, CBGA, and CBDV.

In other embodiments, a method is provided for processing crude cannabis oil to provide a CBGA isolate enriched in CBGA, compared to the starting raw cannabis oil. In some embodiments, the CBGA isolate comprises CBGA in from 70 wt %-99.99 wt %, 75-99.9 wt %, 80-99 wt %, 90-98 wt %, or 95-98 wt % CBGA, or not less than 95 wt %, 97.5 wt %, 98 wt %, 99 wt %, 99.5 wt %, or not less than 99.9 wt % CBGA, while comprising not more than 0.3 wt % of a cannabinoid selected from the group consisting of THC, CBD, CBC, CBG, CBN, THCV, THCA, CBDA, and CBDV.

In other embodiments, a method is provided for processing crude cannabis oil to provide a CBDV isolate enriched in CBDV, compared to the starting raw cannabis oil. In some embodiments, the CBDV isolate comprises CBDV in from 70 wt %-99.99 wt %, 75-99.9 wt %, 80-99 wt %, 90-98 wt %, or 95-98 wt % CBDV, or not less than 95 wt %, 97.5 wt %, 98 wt %, 99 wt %, 99.5 wt %, or not less than 99.9 wt % CBDV, while comprising not more than 0.3 wt % of a cannabinoid selected from the group consisting of THC, CBD, CBC, CBG, CBN, THCV, THCA, CBDA, and CBGA.

In some embodiments, a composition comprising CBD, CBC and terpenes is provided comprising not more than 0.3 wt % of THC.

In some embodiments, a composition comprising CBD and fatty acids is provided comprising not more than 0.3 wt % of THC.

In some embodiments, a composition comprising CBG and CBD is provided comprising not more than 0.3 wt % of THC.

In a specific embodiment, a composition is provided comprising ~65-70% CBD, 0.001-0.5% THC, 0.3-5% CBC, 0.3-5% CBG, 0.3-5% CBN, and ~10-20% fatty acids and terpenes. In some aspects, the composition is dependent on the input hemp extract; however, in the composition the THC content is significantly reduced compared to starting raw cannabis oil such that the composition comprises not more than 0.5%, 0.4%, 0.3%, 0.2% or 0.1% THC, while essentially leaving the profile of the complex mixture intact. In some embodiments, the individual compounds are isolated from the composition and quantified to verify their identity.

In some embodiments of the technology, raw cannabis oil is separated using preparative liquid chromatographic methods described further herein. However, in some embodiments, the eluate fractionation method is non-traditional in order to reconstitute most components of the starting raw cannabis oil to provide a clean cannabis oil, while significantly reducing the amount of THC compared to the starting raw cannabis oil, such that the concentration of THC in the clean cannabis oil is not more than 0.5, 0.4, 0.3, 0.2, 0.1, 0.05, 0.03, 0.01 wt % THC. For example, raw cannabis oil may be injected into a column and eluted in an isocratic, gradient, or a step-wise fashion. Fractions may be taken at (and for) specific column volumes (CVs). These fractions contain one or more compounds from the raw cannabis oil. Additionally, each fraction may be combined with at least one other fraction. Further, each fraction (or combination of fraction) may be concentrated using a variety of techniques as described further herein.

FIG. 1 illustrates a system 100 to perform a liquid chromatographic extraction. As illustrated, FIG. 1 includes a liquid chromatography column 102, a High Performance Liquid Chromatography Mass Spectrometry instrument ("HPLC-MS") 104, and concentration station 108.

In some embodiments, the crude starting cannabis oil, or one or more fractions thereof, is isolated and/or purified by preparative chromatography. Liquid chromatography column 102 includes a column 110. In aspects, the column 110 has a volume of 990 mL, with a height of 291 mm and a diameter of 82 mm. As illustrated, the column 110 is packed with a material 112, such a silica gel for normal phase, or phenyl, C4, C8 or C18 for reverse phase. Additionally, the column may be pre-wet by adding the pre-wetting solvent (such as water, petroleum ether, diethyl ether or ethanol) into the column prior to the injection of cannabis oil sample 114.

The cannabis oil sample 114 may be raw cannabis oil, or hemp oil, obtained from bulk extraction of *Cannabis* spp. plant material. Extraction of cannabis or hemp plant material may be performed using super critical $CO_2$ extraction, liquid-solvent extraction, or other techniques known in the art to provide bulk cannabis oil, also known as crude cannabis oil, or raw cannabis oil. In aspects of the technology, the bulk cannabis oil may contain approximately 30-60% CBD, 3-5% THC, 1-3% CBG, 1-3% CBC, 1-3% CBN, 1-5% CBDA, 1-5% THCA, and 15-30% fatty acids and terpenes.

In some embodiments, raw cannabis oil is first diluted to form the cannabis oil sample 114. For example, for a process employing a normal phase silica gel stationary phase column, the raw cannabis oil may be mixed with a non-polar solvent prior to loading the column. In specific embodiments, the non-polar solvent is hexanes, n-hexane, pentane or petroleum ether. For example, the raw oil can be diluted in a two parts cannabis oil to one part petroleum ether, pentane, hexanes, or n-hexane to form the cannabis oil sample 114. In alternative embodiments, when employing a reverse phase stationary phase column, the raw cannabis oil may be dissolved in ethanol and diluted with water prior to loading to the column. mixed in equal parts with ethanol.

The cannabis oil sample 114 is injected into the column 110 using a pipette or other technique known in the art. In aspects of the technology, the cannabis oil sample 114 is injected into the column 110 in an amount selected from 1 to 20 wt %, 2 to 15 wt % or 4 to 8 wt %, of the stationary phase material by weight. After the cannabis oil sample 114 is injected into the column 110, one or more eluents 116 may be added to the column 110 to extract one or more compounds from the cannabis oil sample 114. A first volume of a first eluent may be added, followed by a second volume of a second eluent and so on. In various embodiments, the eluents are selected from one or more solvents, or one or more binary mixtures of solvents may be used to elute a normal phase column.

In one embodiment, the normal phase column is a silica gel column which may be eluted with a non-polar solvent, a polar solvent, or a a mixture of two or more, three or more, or four or more solvents. In one embodiment, a mixture of one or more non-polar solvents and one or more polar solvents is employed to elute the normal phase column.

In some embodiments, the non-polar solvent may be selected from one or more of pentane, petroleum ether, hexanes, n-hexane, heptane, diisopropyl ether, toluene, chloroform, and methylene chloride. In specific embodiments, the non-polar solvent is petroleum ether, pentane, n-hexane, or a hexane. In embodiments, the non-polar solvent is petroleum ether, a hexane, or n-hexane. In some embodiments, the polar solvent may be selected from one or more of diethyl ether, tetrahydrofuran, ethyl acetate, acetone, acetonitrile, isopropanol, ethanol, and methanol. In specific embodiments, the polar solvent is selected from one or more of diethyl ether, ethanol, methanol, or ethyl acetate. In embodiments, the polar solvent is selected from diethyl ether, a mixture of diethyl ether and ethanol, or ethyl acetate.

In some embodiments, the polar solvent is a mix of from 80-99.9 vol % diethyl ether and 20-0.01 vol % ethanol; a mix of from 90-99 vol % diethyl ether and 10-1 vol % ethanol; or diethyl ether mix of 95% diethyl ether and 5 vol % ethanol. In some embodiments, the polar solvent is diethyl ether. In some embodiments, the polar solvent is ethyl acetate.

In some embodiments, a binary solvent system is employed to elute a normal phase silica gel column using a solvent system selected from petroleum ether/diethyl ether, petroleum ether/diethyl ether mix, hexane/diethyl ether, hexane/diethyl ether mix, or hexane/ethyl acetate. For example, a binary mixture of diethyl ether or a mixture of diethyl ether with ethanol and petroleum ether may be used to elute the column. As used herein, the term "diethyl ether mix" refers to a mixture of 95% diethyl ether and 5% ethanol mixture by volume.

At high altitude, such as in Denver (5280 ft.), it may be desirous to compensate for the decreased atmospheric pressure using low boiling point solvents such as petroleum ether and diethyl ether. For example, the temperature at which the preparative chromatography is performed may be controlled, as well as the pressure, may be controlled to remediate possible discrepancies between "solvent delivered by pump system" and "solvent actually present on column".

In particular, it was observed that, at temperatures above 70 degrees Fahrenheit and high altitude (5280), the pump "sucks" low boiling solvent into its chamber, and the decreased pressure causes a large amount of solvent to vaporize. This apparently ends up filling the pump and line with air bubbles that inhibit reliable and accurate solvent delivery to the chromatography column. In order to minimize this effect, the chromatography may be performed at temperatures below 70 degrees Fahrenheit when in low atmospheric pressure environments. For example, in some embodiments, the preparative chromatography may be performed at a temperature from about 20 to 70 degrees Fahrenheit, 22 to 65 degrees Fahrenheit, 32 to 60 degrees Fahrenheit, or 40 to 55 degrees Fahrenheit. In some embodiments, the chromatography is performed at a cold room temperature from about 22-42 degrees Fahrenheit.

The second specific problem encountered is when diethyl ether contacts silica, the wetting process is slightly exothermic. On a large scale the heat released by this exothermic reaction is enough to vaporize some of the diethyl ether and petroleum ether. This may lead to unreliable and inaccurate solvent delivery to the chromatography column. In order to address this second issue, the solvent gradients must be changed slightly (i.e. from 5% diethyl ether on a small scale to 7% diethyl ether on the large scale) at high low pressure environments. Additionally, the column may be preconditioned for extra column volumes in order to produce consistent separation over multiple runs on a large scale.

As illustrated, a stopcock 118 is actuated to begin flow of the eluent through the packed column. Other means, such as a mechanical actuator, may be used to control the flow.

The eluent 116 may be flowed through the column in a step-wise fashion. For example, the concentration of diethyl ether may be stepped up between the first eluent and the second eluent. In one aspect, for example, a first eluent is 8% diethyl ether mix and 92% petroleum ether (by volume) for 7 column volumes, followed by a second eluent of 30% diethyl ether mix and 70% petroleum ether (by volume) for four column volumes. In another aspect, a first eluent is 4% diethyl ether and 96% petroleum ether (by volume) for 6 column volumes, followed by a second eluent of 8% diethyl ether and 92% petroleum ether (by volume) for four column volumes, followed by a third eluent of 40% diethyl ether and 60% petroleum ether (by volume) for four column volumes. In another aspect, wherein a reverse phase column is employed, the first eluent is 40% $H_2O$ to 60% ethanol (by volume) for 10 CV and the second eluent is 10% $H_2O$ and 90% ethanol (by volume). In other embodiments, a reverse phase column may be eluted used water and one or more of acetonitrile, ethanol, methanol. An acidic modifier such as TFA or formic acid may be added to the water, ethanol, methanol, and/or acetonitrile. It will be appreciated that the flow rate may vary. In some aspects, the flowrate varies based on eluent chosen, the dimensions of the column, and the viscosity of the cannabis oil sample 114. In aspects, where the column volume is 990 mL and the solid phase is silica, the flow rate may be between 100 mL/min and 300 mL/min.

As the extract passes through the column, one through n fractions 118 may be collected, where n is a number representing the number of fractions collected. The n-fractions 118 may be collected at a specific column volume range. For example, one fraction may be collected between 4 and 7 CVs, another fraction may be collected between 8.5 and 9 CVs.

During extraction, liquid chromatography column 102 may be kept at around atmospheric pressure (1 ATM+/−0.2) and around room temperature (22° C.+/−5). FIG. 1 also includes an HPLC-MS 104. In aspects, n-fractions 118 collected using the column 102 may be analyzed. The fractions may first be diluted. For example, a fraction may be diluted Additionally or alternatively, the fractions collected may be first concentrated and/or combined with other fractions prior to being analyzed with the HPLC-MS.

Figure 2:
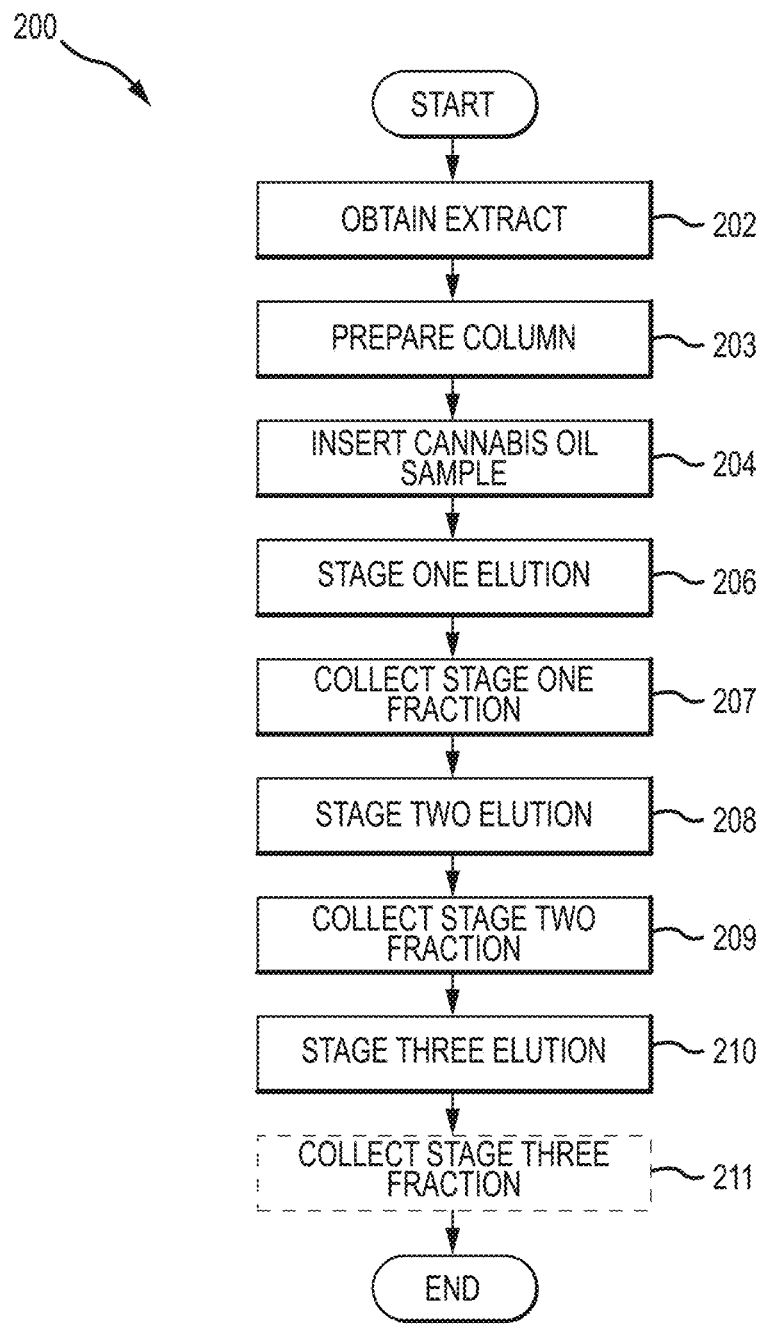
FIG. 2 illustrates a liquid chromatographic method for extracting one or more compounds from raw cannabis oil.

FIG. 2 illustrates a liquid chromatographic method 200 for extracting one or more compounds from raw cannabis oil. Method 200 begins with obtain extract operation 202. In operation 202, raw cannabis oil is extracted from cannabis plant material.

The raw cannabis oil can be obtained by any method known in the art for extraction of *Cannabis* spp. plant material, or the raw cannabis oil can be purchased from a commercial source. For example, the raw cannabis oil can be obtained by supercritical (or subcritical) $CO_2$ method that uses carbon dioxide under high pressure and low temperatures to isolate, preserve and maintain the purity of raw cannabis oil. In one specific embodiment, raw cannabis oil obtained from a supercritical $CO_2$ extraction is used as a starting material for the methods described herein. For example, supercritical $CO_2$ extraction may be performed as described in U.S. Pat. No. 8,895,078, which is incorporated herein by reference in its entirety. Alternatively, a solvent such as petroleum ether, ethanol, methanol, butanol, acetone, dry ice, or olive oil can be used to extract the *Cannabis* spp. plant material, at room temperature (ambient temperature) with stirring, by passive extraction, heated to a temperature above room temperature, or under reflux, as known in the art to provide the raw cannabis oil. In another specific embodiment, raw cannabis oil from a butanol extraction is employed as starting material for methods disclosed herein. Any *Cannabis* spp. plant material can be employed. In some embodiments, the raw cannabis oil is from an extract of *Cannabis sative* L. In some embodiments, the cannabis oil is derived from extraction of *Cannabis* spp. plant material parts selected from one or more of inflorescence of male (staminate) plant, fruiting female (pistillate) plant, staminate flower, stamen, pollen grains, pistillate flower with bract, pistillate flower without bract, seed (archene) with bract, seed without bract, seed without pericarp, leaves, stalks, and roots.

Method 200 then proceeds to prepare column operation 204. In operation 204, a liquid chromatography column is packed. In aspects of the technology, the column described with reference to FIG. 1 is used. It will be appreciated that the column will be packed to compliment the eluent liquid. That is, when a hydrophobic eluent is chosen, the column will be packed with a hydrophilic material, and vice-versa. In aspects, the column is packed with a hydrophilic stationary phase material, such as silica for a normal phase liquid chromatography extraction. Alternatively, a column may be packed with a hydrophobic stationary phase material, such as a carbon 18, phenyl, C4, or C8 reverse phase material.

The column eluate flow is monitored by any known means in the art. In some aspects, the eluate flow is monitored by ultraviolet (UV) absorption, refractive index, thin layer chromatography (TLC), mass spectrometry (MS) total ion detection, or MS mass selective detection. In a particular embodiment, the eluates are monitored by UV and/or mass selective detection. In specific embodiments, the column eluates are monitored by mass selective detection for m/z of one or more of delta-9 tetrahydrocannabinol (THC), tetrahydrocannabinol acid (THCA), cannabidiol (CBD), cannabidiolic acid (CBDA), Cannabigerol (CBG), Cannabichromene (CBC), Cannabinol (CBN), Cannabicyclol (CBL), Cannabivarin (CBV), Tetrahydrocannabivarin (TCHV), Cannabidivarin (CBDV), Cannabichromevarin (CBCV), Cannabigerovarin (CBGV), and Cannabigerol Monomethyl Ether (CBGM). In a specific aspect, eluate is monitored at 315.2 m/z and 345.2 m/z. Monitoring at 315.2 (M+1) will detect CBD and THC, as well as CBC. Monitoring at 345.2 m/z will detect certain other cannabinoid components, for example certain carboxylic acid containing cannabinoid compounds. Unless otherwise specified, percent values refer to weight percent.

Method 200 then proceeds to insert cannabis oil sample operation 208. In aspects, the raw cannabis oil extracted at operation 202 is injected into the column. In other aspects, the raw cannabis oil is first diluted as described above. In a particular embodiment, a column volume of 0.05 CVs of cannabis oil sample may be injected into the column.

Method 200 then proceeds to stage one elution operation 206. In operation 206, a first eluent is added to the column. In aspects, the first eluent is 8% diethyl ether mix and 92% petroleum ether (by volume), 4% diethyl ether and 96% petroleum ether (by volume), or 40% $H_2O$ to 60% ethanol (by volume).

Method 200 then proceeds to collect stage one fractions operation 207. Where the first eluent is 8% diethyl ether mix and 92% petroleum ether (by volume) the first fraction may be collected between 0 and 4 CVs. Where the first eluent 4% diethyl ether and 96% petroleum ether (by volume), the first fraction may be collected between 0 and 2 CVs, and the second fraction may be collected between 2 and 6 CVs. Further, where the first eluent is 40% $H_2O$ to 60% ethanol (by volume), the first fraction may be collected between 0 and 4 CVs, and the second fraction may be collected between 4 and 7 CVs.

Method 200 then proceeds to stage two elution operation 208. In operation 208, a second eluent is added to the column. In one aspect, a second eluent is 30% diethyl ether mix and 70% petroleum ether (by volume), 8% diethyl ether mix and 92% petroleum ether (by volume), or second eluent is 10% $H_2O$ and 90% ethanol (by volume).

Method 200 then proceeds to collect stage two fractions operation 209. Where the second eluent is 30% diethyl ether mix and 70% petroleum ether (by volume) the second fraction may be collected between 4 and 8 CVs, the third fraction may be collected between 8.5 and 9 CVs, the fourth fraction may be collected between 9 and 9.5 CVs the fourth fraction may be collected between 9.5 and 10 CVs, and the fifth fraction may be collected between 10 and 13 CVs. Where the first eluent 8% diethyl ether and 92% petroleum ether (by volume), the third fraction may be collected between 7 and 9.5 CVs. Further, where the first eluent is 10% $H_2O$ to 90% ethanol (by mass), the first fraction may be collected between 7 and 9 CVs the fourth fraction may be collected between 9 and 12 CVs.

Method 200 optionally proceeds to stage three elution operation 210. In operation 210, a third eluent is added to the column. In aspects of the technology, a third eluent of 40% diethyl ether and 60% petroleum ether (by volume) is added.

Method 200 then optionally proceeds to collect stage three fractions operation 211. Where the third eluent of 40% diethyl ether and 60% petroleum ether (by volume), the fourth fraction may be collected between 9.5 and 14 CVs.

Figure 3:
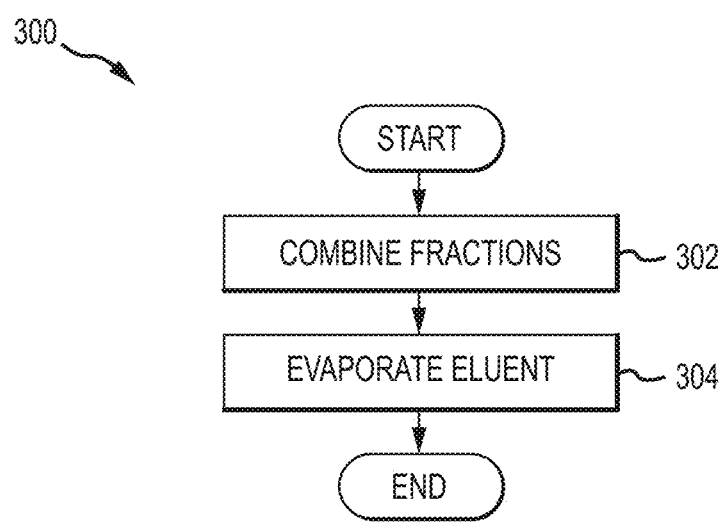
FIG. 3 illustrates a method for concentrating one or more fractions.

FIG. 3 illustrates a method 300 for concentrating one or more fractions. Method 300 begins with combine fractions operation 302. In some embodiments, the normal phase column first eluent is 8% diethyl ether mix in 92% petroleum ether and is run at a rate of 200 mL/min. After 4 CV (3960 mL where the column volume is 990 mL), a second eluent of 30% diethyl ether mix and 70% petroleum ether (by volume) may then be added to the column. In aspects, 120 ml fractions are collected. In one embodiment, eluate from 1-4 CV and 9-20 CV are collected, pooled, evaporated and combined to provide a clean cannabis oil having 60-70% CBD and not more than 0.3% THC. Additionally, fractions 4-8 may be separately combined, evaporated, and optionally recrystallized to provide a CBD isolate from any appropriate solvent, e.g., n-hexane, or pentane.

Operation then proceeds to evaporate eluent operation 304. In evaporate eluent operation, the eluent is evaporated from the extract. In some embodiments, the eluent is removed in vacuo. In aspects, the combined fractions described above with reference to operation 302 are exposed to an environment of 0.3 ATMs, a temperature of 45 degrees Celsius, and agitated. In other aspects, each fraction is concentrated prior to combination. Operation 304 may continue until one or more compounds precipitates from the combined liquid fraction.

FIGS. 4-9 illustrate various analytical HPLC-MS chromatograms. To generate each chromatogram, a single-quad MS detector rather was used. The total ion chromatogram as well as two specific masses: 315.2 amu and 345.2 amu were monitored.

Figure 4A:
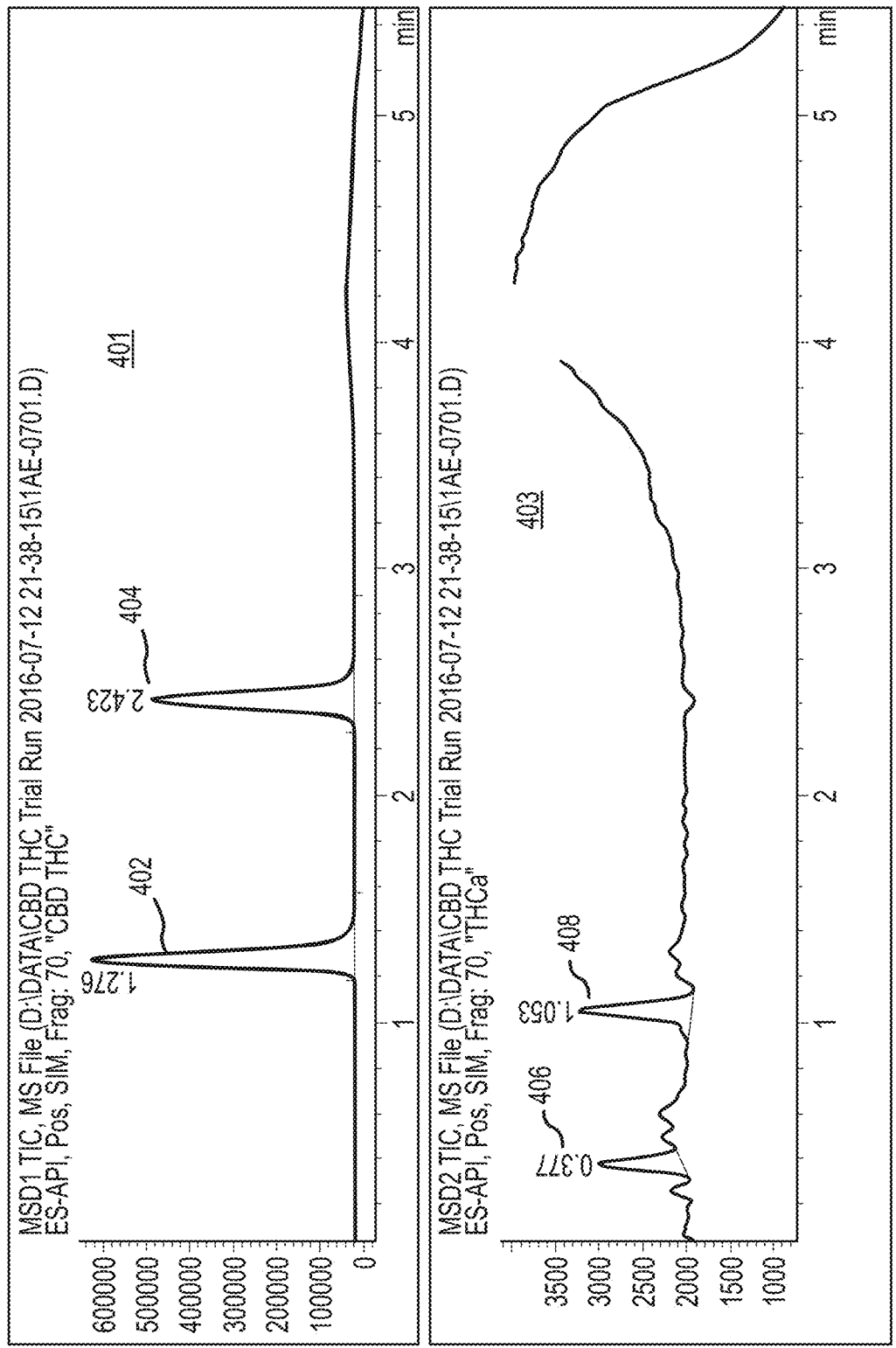

FIGS. 4A and 4B illustrate analytical HPLC-MS chromatograms 401 and 403, of standards of a combined CBD and THC monitored at m/z 315.2 (M+H). The samples of the CBD and THC were obtained as commercial standards (Sigma-Aldrich). Illustrated in the chromatogram 401 is CBD peak 402 and THC peak 404. As illustrated in chromatogram 401, the CBD peak 402 has a retention time of about 1.3 min, and the THC peak 404 has a retention time of about 2.4 minutes. Further, illustrated in chromatogram 403 monitored at m/z 345.2, shows certain very minor cannabinoid components eluting at peaks 406 (with a retention time of around 0.4 minutes) and 408 (with a retention time of around 1.1 minutes).

Figure 5A:
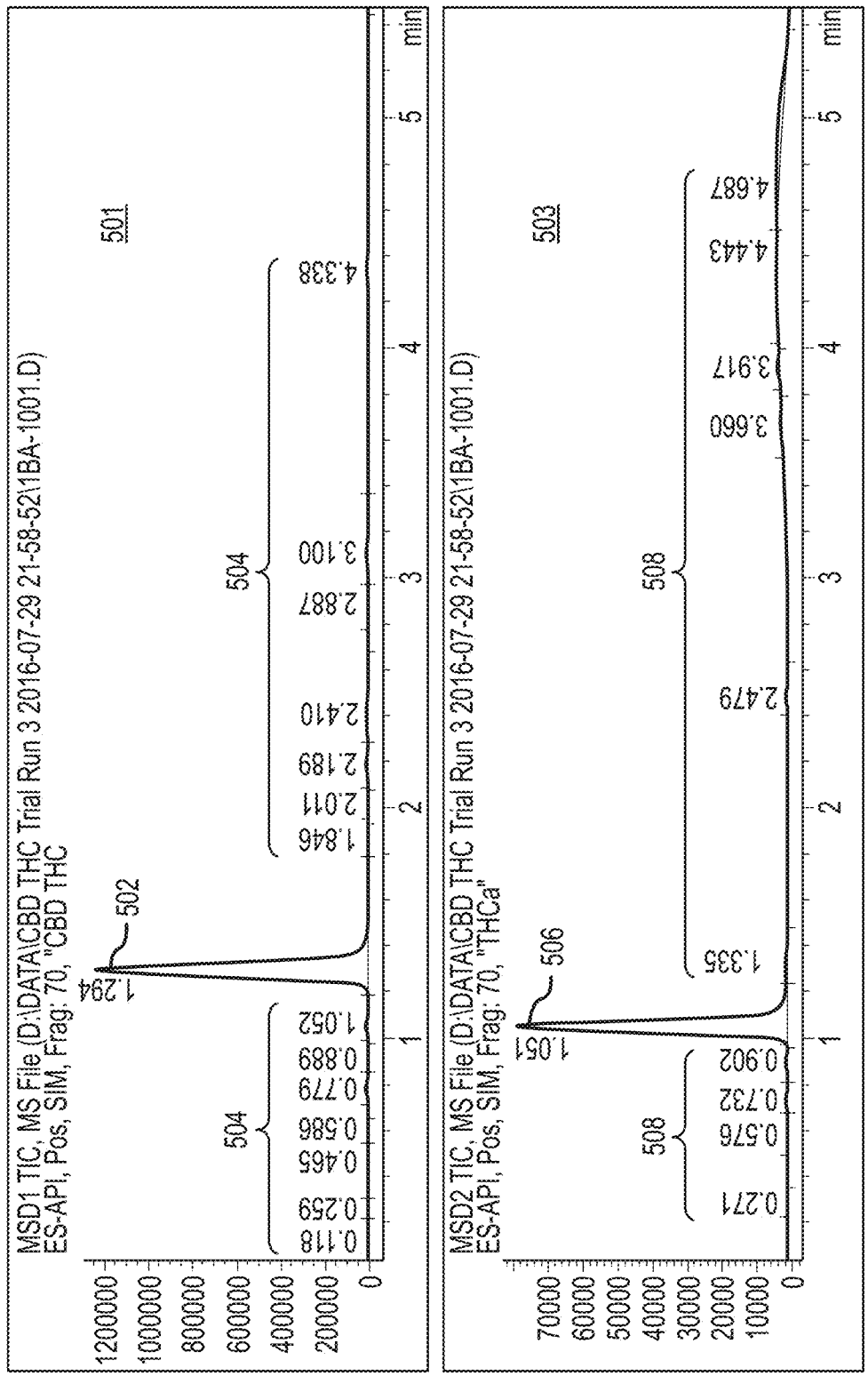

FIGS. 5A and 5B are an HPLC-MS chromatogram 500 of crude cannabis oil. The crude oil of this sample was prepared using a supercritical $CO_2$ extraction method. The sample was prepared by mixing raw cannabis oil with a diluting solvent. As illustrated, FIGS. 5A and 5B include two HPLC-MS chromatograms, namely, a first chromatogram 501 monitored at m/z 315.2 and a second chromatogram 503 monitored at m/z 345.2. The first chromatogram 501 illustrates a peak 502 at around 1.3 mins retention time. By comparing the peak 502 to the CBD peak 402 illustrated in FIGS. 4A and 4B, it will be appreciated that peak 502 illustrates the CBD peak. The amount 510 of peak 502 is 64%. Additionally illustrated in chromatogram 501 are other minor peaks 504. Other peaks 504 represent various other compounds present in the bulk cannabis oil.

Second chromatogram 503 illustrates peak 506, at m/z 345.2 (M+H). Additionally illustrated in second chromatogram 503 is other peaks 508, which represents other compounds contained in the raw cannabis sample.

Figure 6A:
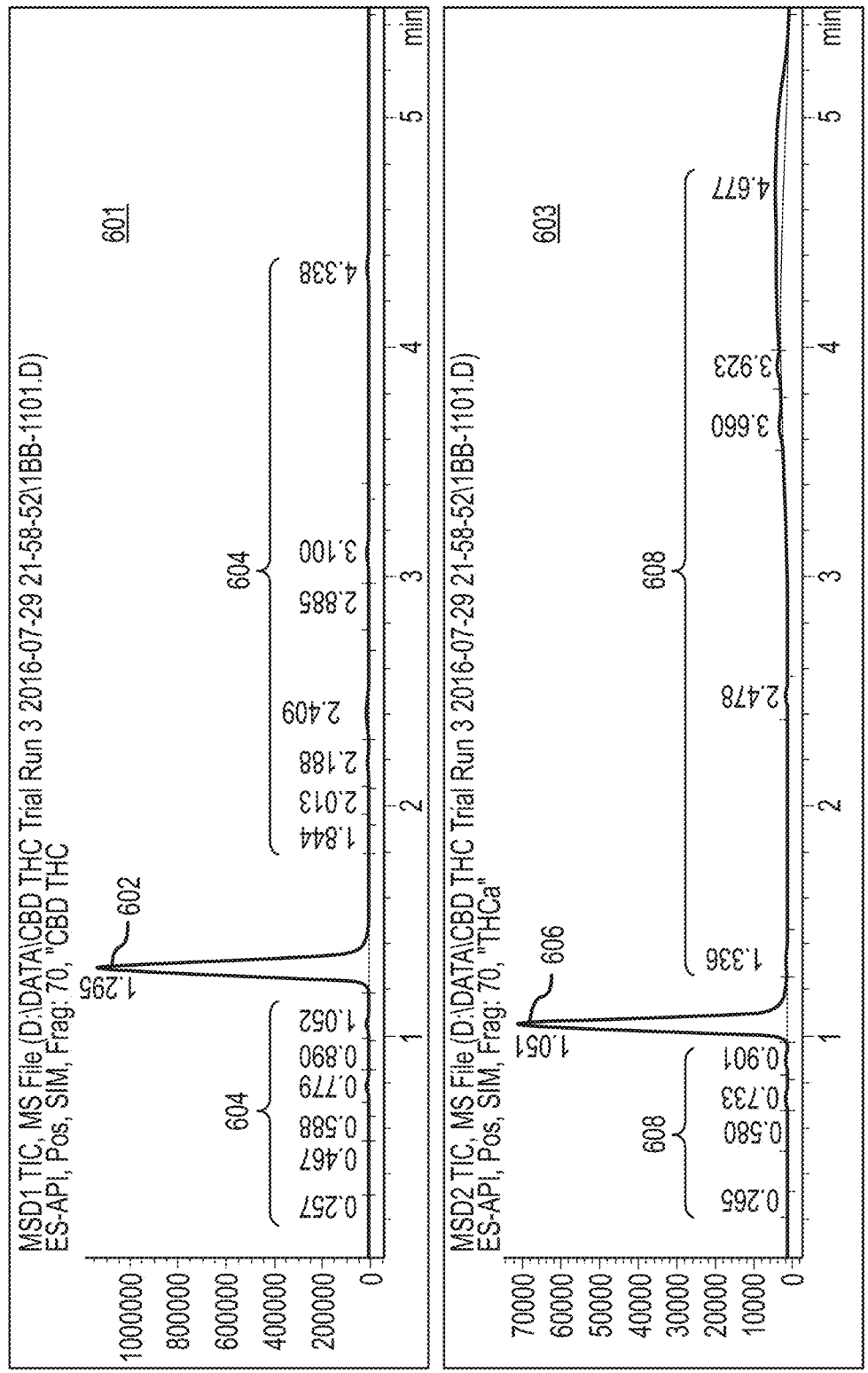

FIGS. 6A and 6B illustrate HPLC-MS chromatograms 601 and 603 of raw cannabis oil. The raw cannabis oil is same starting material as the raw cannabis oil referenced with respect to FIGS. 5A and 5B, but the raw cannabis oil has been diluted. As illustrated, FIGS. 6A and 6B include two HPLC-MS Chromatograms, a first chromatogram 601 and a second chromatogram 603. The first chromatogram 601 illustrates a peak 602 at around 1.3 mins retention time. By comparing the peak 602 to the CBD peak 402 illustrated in FIGS. 4A and 4B, it will be appreciated that peak 602 illustrates a CBD peak. Additionally illustrated in chromatogram 601 is other peaks 604. Other peaks 604 represent various other compounds present in the bulk cannabis oil. The amount 610 of peak 602 is around 65%.

Second chromatogram 603 illustrates peak 606 at m/z 345.2 (M+H). Additionally illustrated in second chromatogram 603 are other peaks 608, which represents other compounds contained in the raw cannabis sample.

Figure 7A:
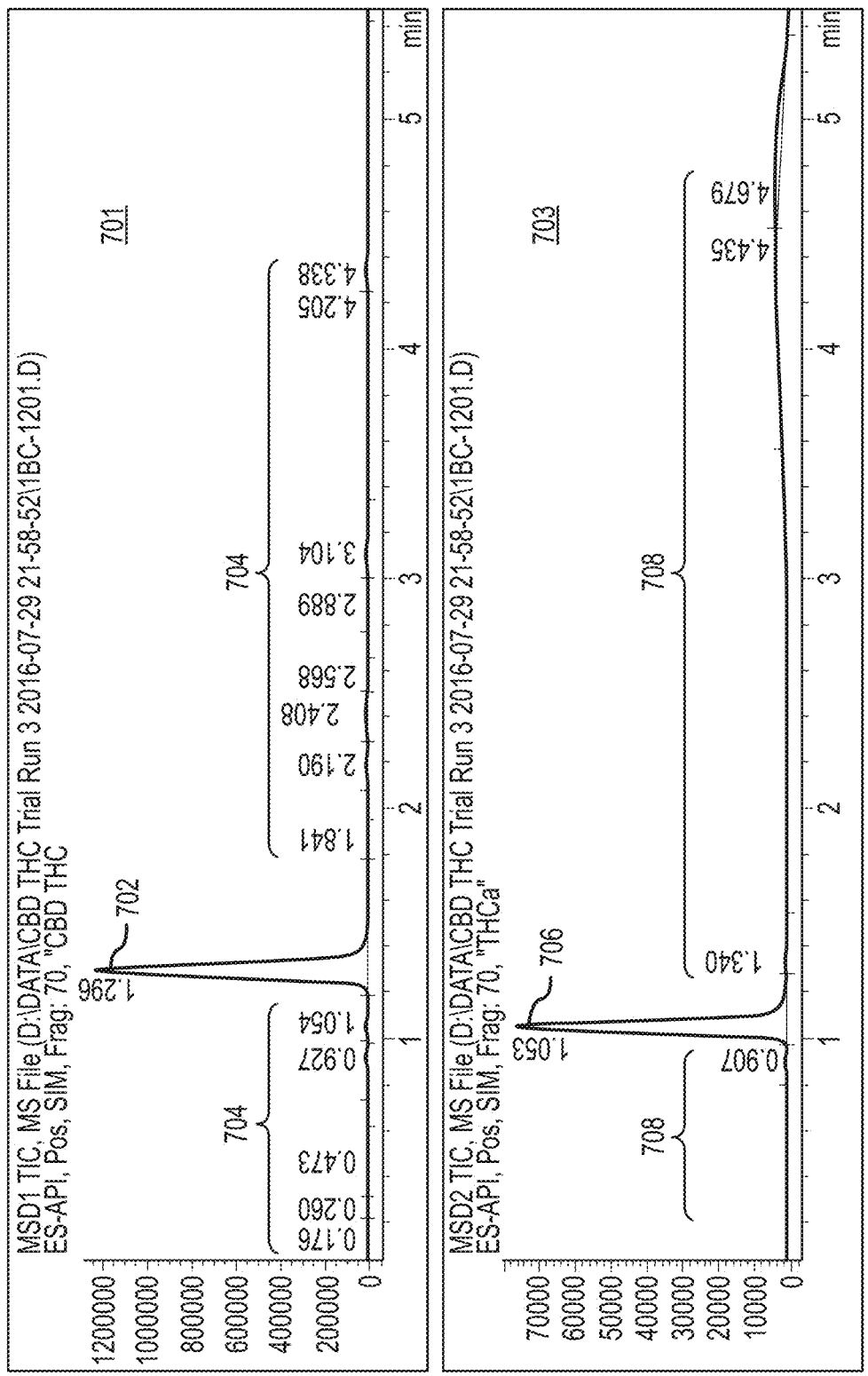

As illustrated, FIGS. 7A and 7B include two HPLC-MS Chromatograms of the clean cannabis oil obtained in Example 1, namely, a first chromatogram 701 and a second chromatogram 703. The first graph 701 illustrates a peak 702 at around 1.3 mins retention time. By comparing the peak 702 to the CBD peak 402 illustrated in FIGS. 4A and 4B, it will be appreciated that peak 702 illustrates a CBD peak. Additionally chromatogram 701 includes other peaks 704. Other peaks 704 represent various other compounds present in the clean sample oil. The amount 710 of peak 702 is around 68%.

Second chromatogram 703 illustrates peak 706 at m/z 345.2 (M+H). Additionally illustrated in second chromatogram 703 is other peaks 708, which represents other compounds contained in the raw cannabis sample.

Figure 8A:
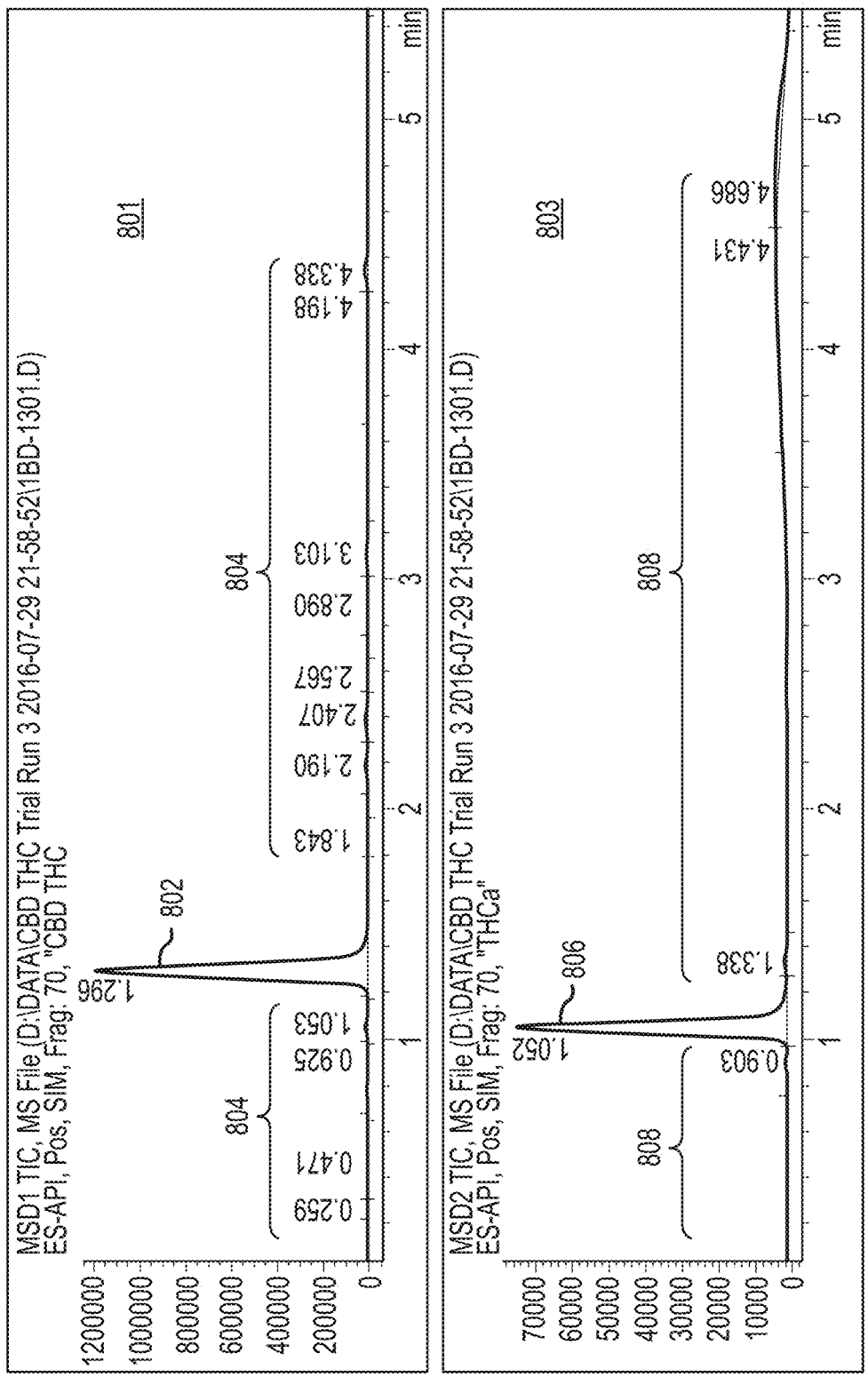

FIGS. 8A and 8B illustrate HPLC-MS chromatograms for a combined and diluted sample of clean cannabis oil of Example 1. The cannabis oil sample was the same as the cannabis oil sample referenced with respect to FIGS. 7A and 7B, but has been further diluted. Dilution occurred by addition of a solvent prior to analytical HPLC. As illustrated, FIGS. 8A and 8B include two HPLC-MS Chromatograms, namely, a first chromatogram 801 and a second chromatogram 803. The first chromatogram 801 illustrates a peak 802 at around 1.3 mins retention time. Comparing the peak 802 to the CBD peak 402 illustrated in FIGS. 4A and 4B, it will be appreciated that peak 802 illustrates the CBD peak. Additionally, chromatogram 801 includes other peaks 804. Other peaks 804 represent various other compounds present in the bulk cannabis oil. The area 810 of peak 802 is around 69%.

Second chromatogram 803 illustrates peak 806 at m/z 345.2 (M+H). Additionally illustrated in second chromatogram 603 are other peaks 608, which represents other compounds contained in the cannabis oil sample.

Figure 9A:
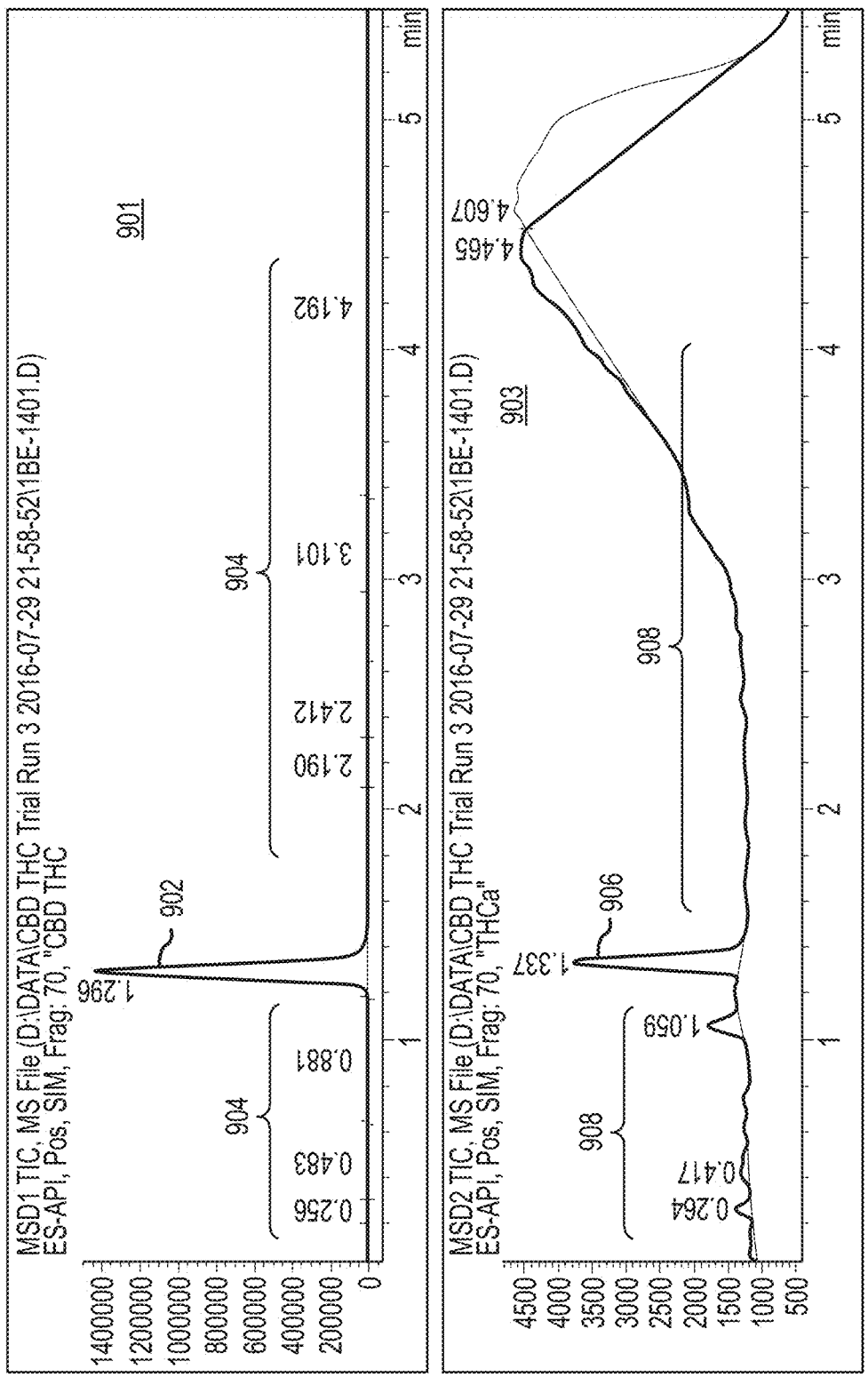

As illustrated, FIGS. 9A and 9B include two HPLC-MS chromatograms, a first chromatogram 901 and a second chromatogram 903. The first chromatogram 901 illustrates a peak 902 at around 1.3 mins retention time. By comparing the peak 902 to the CBD peak 402 illustrated in FIGS. 4A and 4B, it will be appreciated that peak 902 illustrates the CBD peak. Additionally, chromatogram 901 includes other peaks 904. Other peaks 904 represent various other compounds present in the cannabis oil sample. The area 910 of peak 902 is around 95.1%.

Second chromatogram 903 illustrates minor peak 906 at m/z 345.2 (M+H). Additionally illustrated in second chromatogram 903 are other minor peaks 908, which represents other compounds contained in the cannabis oil sample.

Example 1. Normal Phase Preparative Method 1

In this example, a Biotage Isolera Flash Chromatography System was employed to process raw cannabis oil to deplete THC component to provide clean cannabis oil, and further to provide CBD isolate. HPLC purity of starting crude cannabis oil used herein was 60.50% CBD and 3.50% THC.

Figure 10:
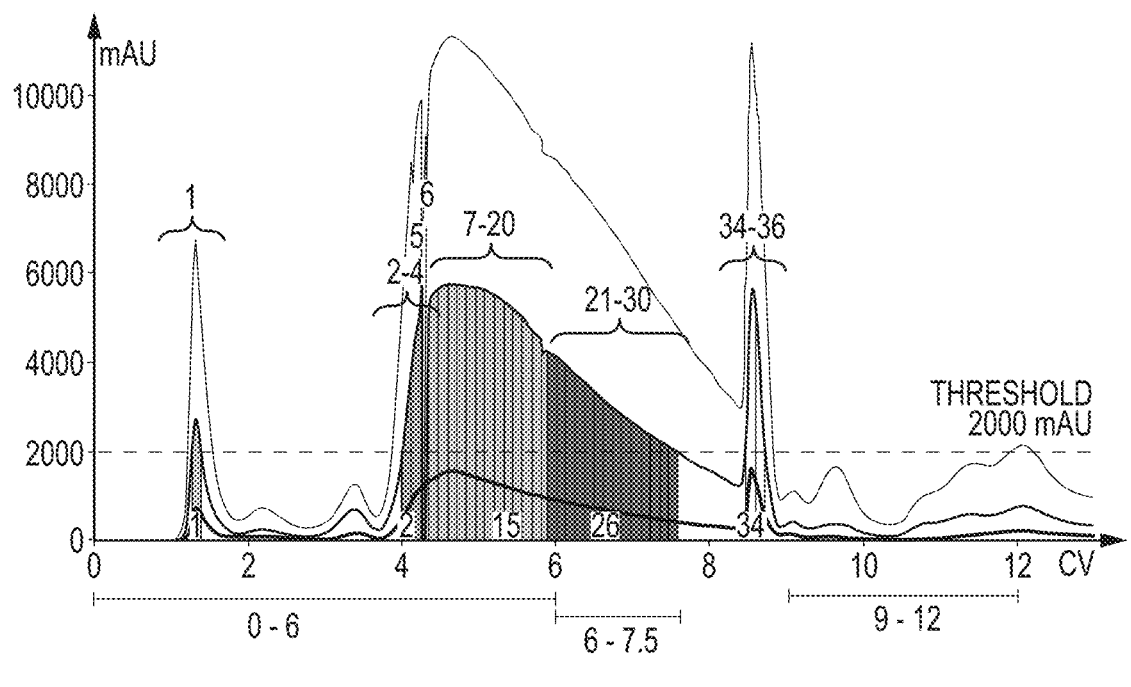
FIG. 10 illustrates a preparative chromatogram of a normal phase separation method monitored at 220 nm and 240 nm where eluate from 0-6 CVs is pooled with 9-12 CVs to provide a clean cannabis oil following rotoevaporation, where the clean cannabis oil exhibits about 68% CBD and not more than 0.3% THC. Fractions 21-30, or about 6-7.5 CVs are pooled, evaporated, and recrystallized to provide a CBD isolate with about 95.1% CBD, as shown in Example 1.
Figure 10:
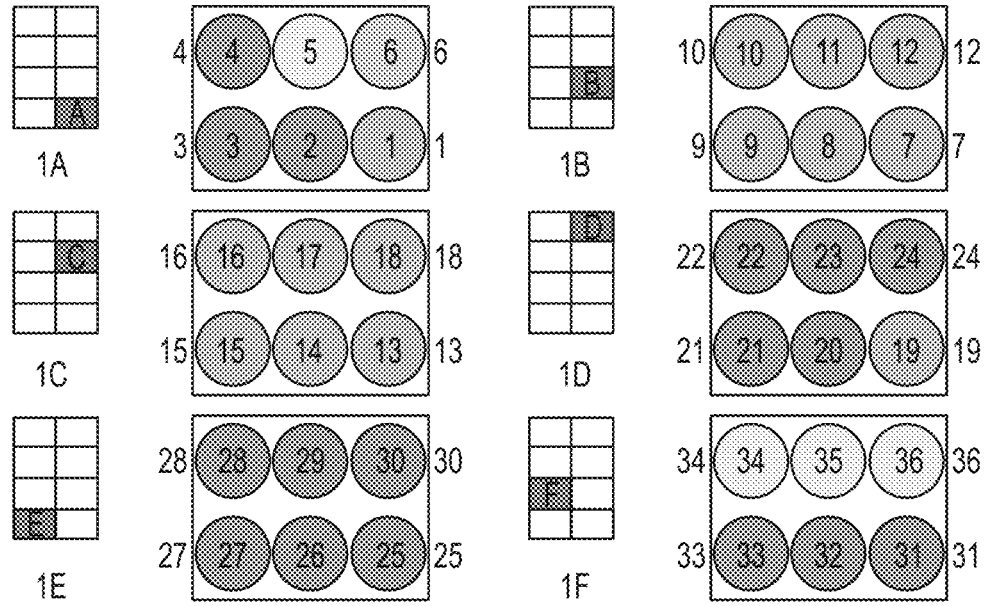
Figure 11:
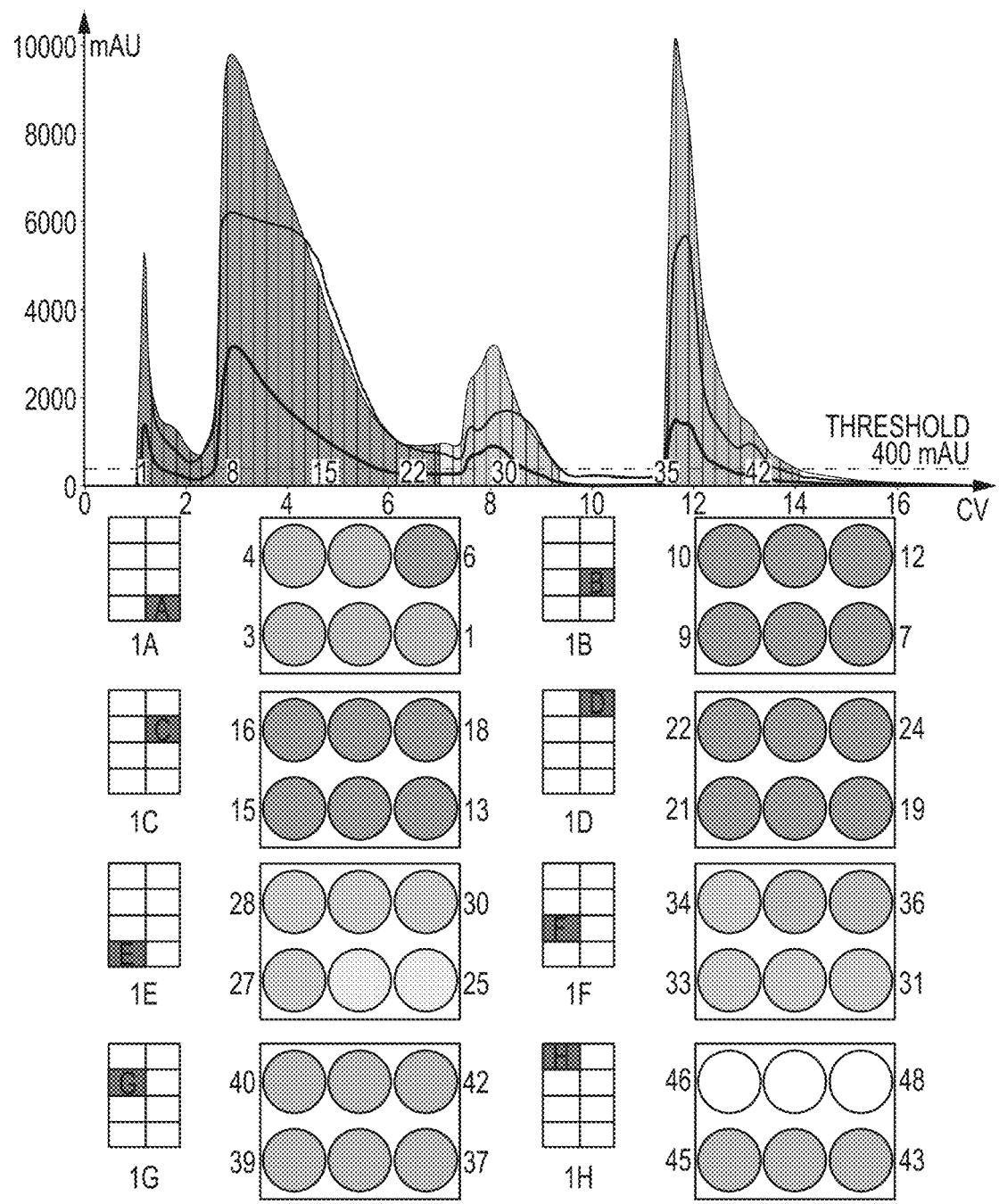
FIG. 11 illustrates a preparative chromatogram of a normal phase separation method of raw cannabis oil described in Example 2.
Figure 12:
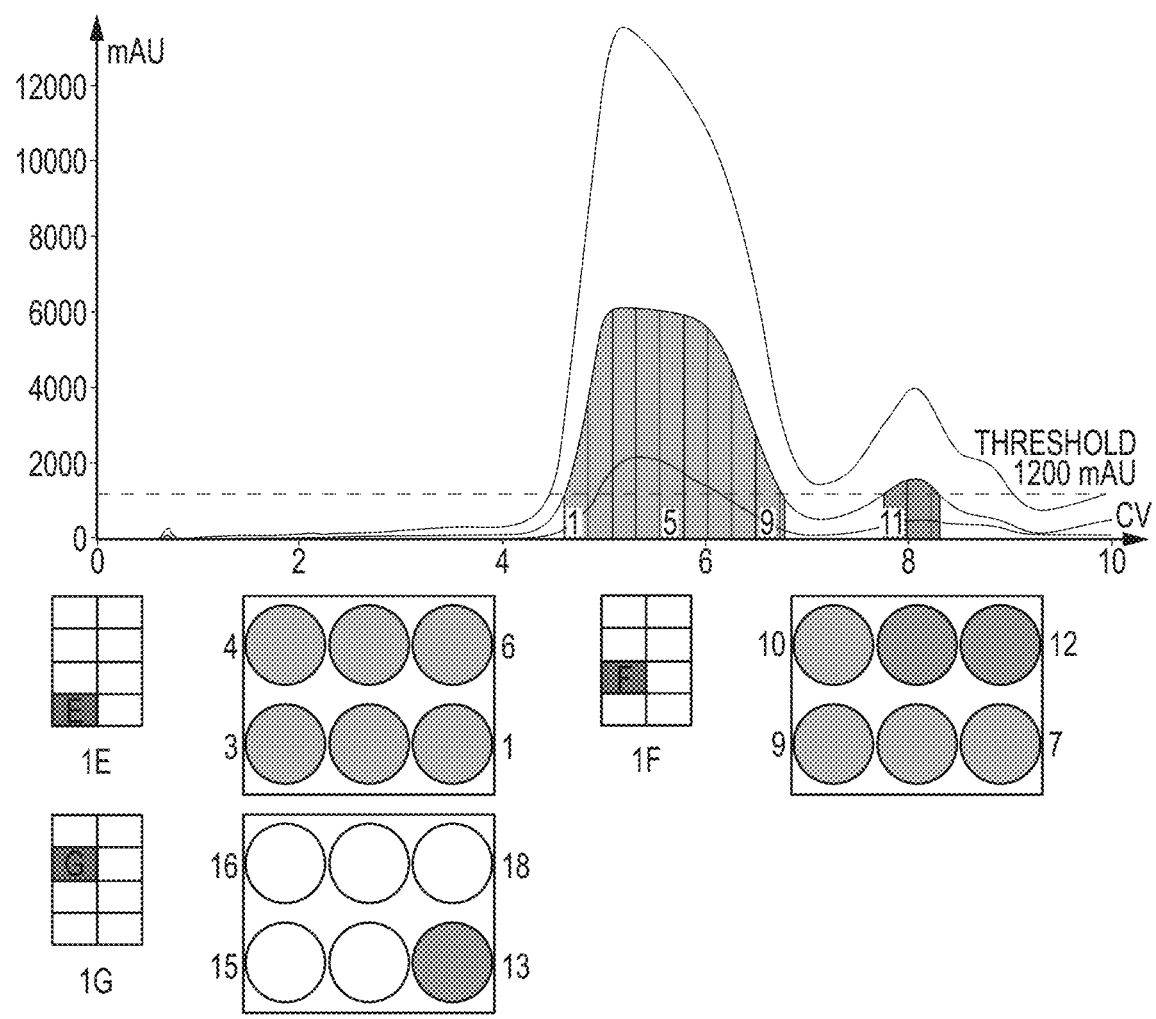
FIG. 12 illustrates a preparative reverse phase separation method of raw cannabis oil described in Example 3.

45 g hemp oil (injection mass 6 wt %) was dissolved in 22.5 mL petroleum ether and injected to a 750 g normal phase silica gel column (SNAP KP-Sil 750 g, BIOTAGE) and rinsed with pet ether for a total injection volume of 67.5 mL. Solvent A was petroleum ether; Solvent B was 95% diethyl ether and 5% ethanol. Solvents A and B were employed to elute the column in a step gradient of 8 vol % B run for 7 column volumes, increased from 8-30 vol % B for 0 column volume, then 30 vol % B for 6 column volumes at a flow rate of 200 mL/min. The column eluate was monitored by UV-vis at 220 nm, and 240 nm, as shown in FIG. 10. 120 mL fractions were collected. Following elution, the peak fractions were subjected to analytical HPLC or TLC analysis. Appropriate fractions were combined and solvents removed by rotoevaporation. Analytical HPLC by the method of Example 4 was employed to determine relative amounts of cannabinoids of interest.

As shown in FIG. 10, all eluate before 4 CV, fractions 1-20, (~1-6 CV) and all eluate from 9-12 CV were pooled and concentrated to make isolate 1. Following evaporation of solvents from isolate 1, clean oil was obtained in about a 70 wt % crude yield. This is a result of conservative fraction collection and the loss of THC and minor portions of contaminated CBC. HPLC purity of clean cannabis oil was 69% CBD and <0.3% THC as shown in FIGS. 7 and 8.

Fractions 21-30 were collected, pooled and concentrated to make isolate 2. Isolate 2 was about 25 wt % of the starting material. Isolate 2 was either sold as is, recrystallized to further purify, or added back to clean oil in about a 1:2 ratio to increase the yield of clean oil to 90-95% from starting crude. HPLC purity of purified isolate is 95% CBD and <0.3% THC, as shown in FIG. 9.

Example 2. Normal Phase Preparative Method 2

In this example, a Biotage Isolera Flash Chromatography System was employed to process raw cannabis oil to deplete THC component. In this example, a Biotage Isolera Flash Chromatography System was employed to process raw cannabis oil to deplete THC component. 45 g hemp oil (injection mass 6 wt %) was dissolved in 22.5 mL petroleum ether and injected to a 750 g normal phase silica gel column (SNAP KP-Sil 750 g, BIOTAGE) and rinsed with pet ether for a total injection volume of 67.5 mL. Solvent A was petroleum ether; Solvent B was 99.9% diethyl ether. Solvents A and B were employed to elute the column at 200 mL/min in a step gradient of 4 vol % B for 6 column volumes, then 8 vol % B for 4 column volumes, then 40 vol % B for 4 column volumes. Eluate was monitored at 220 nm and 240 nm. 120 mL fractions were collected. Following elution, the peak fractions were subjected to analytical HPLC or TLC analysis. Fractions 1-20 (1-6 CV) and 36-45 (11.5-14 CV) were combined and solvents removed by rotoevaporation. Analytical HPLC was employed to determine relative amounts of cannabinoids of interest.

Example 3. Reverse Phase Preparative Method 3

In this example, a Biotage Isolera Chromatography System was employed using a preparative Reverse Phase C18 column to process raw cannabis oil. 8.0 g hemp oil (injection mass 2 wt %) was dissolved in 16 mL ethanol and injected to a 400 g RP C18 column (SNAP C18 400 g) and rinsed with ethanol for a total injection volume of 24 mL. Solvent A was water; Solvent B was ethanol. Solvents A and B were employed to elute the column at 100 mL/min in a gradient of 60-90 vol % B (ethanol/formic acid) over 10 column volumes. Column eluate was monitored at 220 nm, and 100 mL fractions were collected. Following elution, the peak fractions were subjected to analytical HPLC or TLC analysis. Appropriate fractions were combined and solvents removed by rotoevaporation. Analytical HPLC was employed to determine relative amounts of cannabinoids of interest.

Example 4. Reverse Phase Analytical HPLC Method

Raw cannabis oil and process samples were evaluated by HPLC, or HPLC-MS by diluting sample at 60 uL/6 mL with an injection volume of 1 uL. Solvent A is water 0.1% formic acid; Solvent B is acetonitrile 0.1% formic acid. The C18 analytical column (Agilent Eclipse Plus C-18/RRHD 1.8 um 21×50 mm) is run at 50° C., at 0.5 mL/mn in a gradient elution of 70% B from 0-3 minutes, then 70-95% B from 3-5 min. HPLC-MS employed dual ion monitoring using ES-API, positive ion monitoring at 315.2 amu (Signal 1, MSD1) and 345.2 amu (Signal 2, MSD2). FIGS. 4-9 illustrate various analytical HPLC-MS chromatograms. To generate each chromatogram, a single-quad MS detector rather was used. The total ion chromatogram as well as two specific masses: 315.2 amu and 345.2 amu. Calibration curves developed from external reference standards for Cannabidiol (CBD) (Sigma-Aldrich), and d9-THC (Sigma-Aldrich). Using this method, HPLC purity of crude cannabis oil used herein was 60.50% CBD and 3.50% THC. HPLC purity of purified clean cannabis oil from Method 1 was was 69% CBD and <0.3% THC. HPLC purity of purified isolate from Method 1 was 95% CBD and <0.3% THC, as discussed in Example 1.

Example 5. Production Normal Phase CBD Isolate Method

The following protocol of Example 5 has been used:
Preparation:
1. Dissolve 750 g of crude oil in 400 mL of petro ether. Use "gentle" heating and cap with foil with a large stir bar. Record sensory characteristics of starting material description (color, consistency, smell, etc.) and record actual mass of starting material (g).
2. Once everything is dissolved, let crude oil mixture cool to room temperature and make sure everything is liquid. There should be about 1200 mL of total mixture in the syringes. Record the total volume of mixture prior to injection (mL) and the description of injection material (color, consistency).
3. Prepare 3 gradient tanks: a. G1: 6% ethyl ether in petroleum ether (3.6 L of ethyl ether in 56.4 L of petroleum ether); b. G2: 15% ethyl ether in petroleum ether (9 L of ethyl ether in 51 L of petroleum ether); and c. G3: 80% ethyl ether in petroleum ether (48 L of ethyl ether in 12 L of petroleum ether).
4. Turn on column compression and set to ~100 PSI.
5. Run G1 for 1.5 CV (13 L) to condition the 5 kg column. Collect the solvent from this run in a "recycle" solvent container. Solvent pressure should be between 30-35 PSI and flowing at ~1 L per minute.
6. Load sample. Increase pressure to ~80 PSI to load sample faster. Record Load time (min).
7. Decrease solvent pressure back to 30-35 PSI. Begin running G1 solvent again.
Collection:
8. Initial collection: a. Collect 1 CV (9 L) of solvent in a 10 L carboy labelled A. (If yellow color is observed before 9 L switch solvent line to a new carboy immediately.) Record volume of solvent before yellow observed (L). b. Collect an additional 0.5 CV (4 L) in a 10 L carboy labelled B.
9. Fraction collection: Notes: All fractions are 6 L. Collect all fractions in 10 L carboys.
 a. Collect 1 CV (1 fraction). (6 L).
 b. After Fraction 1 stop solvent flow and switch to G2 ISO.
 c. Continue collecting fractions.
 d. After Fraction 7 stop solvent flow and switch to G3.
 e. Collect Fractions 8, 9, and 10. (If solvent is still colored yellow after fraction 10 collect additional fractions.
Analysis:
10. Run TLC on fractions to determine CBD containing fractions for crystallization, disposal, and recombination. Collected and record each of isolate fractions, raffinate fractions, THC disposal fractions, collected cannabinoid fractions. Record description of isolated fractions (approx. volume, color). Record description of raffinate fractions (approx. volume, color).
Raffinate Concentration:
11. Collect raffinate fractions in a preweighed 20 L flask. Concentrate raffinate fractions under reduced pressure. Set vacuum to 0 mtorr and bath to 55° C. Keep this raffinate for future use. Record Mass of flask (g). Record Description of concentrated raffinate oil (color, consistency). Mass of raffinate oil (g).

Cannabinoid Concentration:

12. Collect cannabinoid fractions in a preweighed 20 L flask. Concentrate cannabinoid fractions under reduced pressure. Set vacuum to 0 mtorr and bath to 65° C. Keep these cannabinoids for future use. Record mass of flask (g), description of concentrated cannabinoids (color, consistency), and mass of cannabinoid oil (g).

Crystallization:

13. Tare a 5 L round bottom flask. Concentrate isolate fractions under reduced pressure. Set vacuum to 0 mtorr and bath to 65° C. Record Mass of flask (g), and mass of isolate R1 (g).

14. Dissolve isolate R1 in 2×(mass of isolate R1) in mL of hot hexanes. Record volume of hot hexanes used (mL).

15. Seed crystallization dish with enough crystals to sparsely cover the bottom of the container. Cover crystallization dish with foil and place in freezer at 30° F. for 12 h.

16. Decant crystallization dish and rinse crystals with cold hexanes. The decanted solution and rinse hexanes should be collected and labelled "mother liquor". Collect and mass rinsed crystals that remain in the tray. These crystals will be labelled isolate R2. Record Description of mother liquor/rinse combination (color). Description of isolate R2 (color, consistency). Mass of isolate R2 (g).

17. Dissolve isolate R2 in ~2×(mass of isolate R2) in mL of hot hexanes.

18. Seed crystallization dish with enough crystals to sparsely cover the bottom of the container. Cover with foil and let crystallize for 12 h at room temperature. Record room temperature (° F.).

19. Decant new mother liquor and rinse crystals with cold petroleum ether. This rinse and decanted material should be combined with "mother liquor" from Step 16.

20. Collect the crystals remaining in tray and crush using mortar and pestle. Labelled this material isolate F. Mass isolate F right after grinding. Record Description of final crystals (color, consistency). Record Mass of isolate F post grinding (g).

21. Dry isolate F under reduced pressure or in a vacuum oven at 50° C. Record Description of isolate F (color, consistency). Record Mass of isolate F post drying (g).

Example 6. Production THC Removal Method

The following protocol of Example 6 has been used:
Preparation:
1. Dissolve 500 g of crude oil in 250 mL of petro ether. Use "gentle" heating and cap with foil with a large stir bar. Record Starting material description (color, consistency, smell, etc.). Record Mass of starting material (g).

2. Once everything is dissolved, let crude oil mixture cool to room temperature and make sure everything is liquid. There should be about 750 mL of total mixture in the syringes. Record Total volume of mixture prior to injection (mL). Record Description of injection material (color, consistency).

3. Prepare 3 gradient tanks:
  a. G1: 6% ethyl ether in petroleum ether (3.6 L of ethyl ether in 56.4 L of petroleum ether);
  b. G2: 12% ethyl ether in petroleum ether (7.2 L of ethyl ether in 52.8 L of petroleum ether); and
  c. G3: 80% ethyl ether in petroleum ether (48 L of ethyl ether in 12 L of petroleum ether).

4. Turn on column compression and set to ~100 PSI.

5. Run G1 for 1.5 CV (13 L) to condition the 5 kg column. Collect the solvent from this run in a "recycle" solvent container. Solvent pressure should be between 30-35 PSI and flowing at ~1 L per minute.

6. Load sample. Increase pressure to ~80 PSI to load sample faster. Record Load time (min).

7. Decrease solvent pressure back to 30-35 PSI. Begin running G1 solvent again.

Collection:
8. Initial collection: d. Collect 1 CV (9 L) of solvent in a 10 L carboy labelled A. (If yellow color is observed before 9 L switch solvent line to a new carboy immediately.) Record volume of solvent before yellow observed (L). e. Collect an additional 1 CV (9 L) in a 10 L carboy labelled B.

9. Fraction collection:
  f. Collect 4 CV (36 L) in 2 L fractions. (18 fractions).
  g. After Fraction 18 stop solvent flow and switch to G2.
  h. Continue collecting Fractions in 2 L portions.
  i. After fraction 31 stop solvent flow and switch to G3.

10. Final Fraction Collection:
  j. After Fraction 36 switch collection to 10 L carboys.
  k. Collect two 8 L fractions labelled X and Y. (If solvent is still colored yellow after fraction Y collect an additional 8 L fraction labelled Z.)

Analysis:
11. Run TLC on fractions to determine CBD containing fractions for crystallization, disposal, and recombination. Record Collected isolate fraction number. Record Collected raffinate fraction numbers. Record Collected disposal fraction numbers. Record Description of isolation fractions (approx. volume, color). Record Description of raffinate fractions (approx. volume, color).

Raffinate Concentration:
12. Collect raffinate fractions in a preweighed 20 L flask. Concentrate raffinate fractions under reduced pressure. Set vacuum to 0 mtorr and bath to 55° C. Record Mass of flask (g). Record Description of concentrated raffinate oil (color, consistency). Record Mass of raffinate oil (g).

Crystallization:
13. Tare a 5 L round bottom flask. Concentrate isolate fractions under reduced pressure. Set vacuum to 0 mtorr and bath to 65° C. Record Mass of flask (g). Record Mass of isolate R1 (g).

14. Dissolve isolate R1 in 2×(mass of isolate R1) in mL of hot hexanes. Record Volume of hot hexanes used (mL).

15. Seed crystallization dish with enough crystals to sparsely cover the bottom of the container. Cover crystallization dish with foil and place in freezer at 30° F. for 12 h.

16. Decant crystallization dish and rinse crystals with cold hexanes. The decanted solution and rinse hexanes should be collected and labelled "mother liquor". Collect and mass rinsed crystals that remain in the tray. These crystals will be labelled isolate R2. Record Description of mother liquor/rinse combination (color). Record Description of isolate R2 (color, consistency). Record Mass of isolate R2 (g).

17. Dissolve isolate R2 in ~2×(mass of isolate R2) in mL of hot hexanes.

18. Seed crystallization dish with enough crystals to sparsely cover the bottom of the container. Cover with foil and let crystallize for 12 h at room temperature. Record Room temperature (° F.).

19. Decant new mother liquor and rinse crystals with cold petroleum ether. This rinse and decanted material should be combined with "mother liquor" from Step 16.

20. Collect the crystals remaining in tray and crush using mortar and pestle. Labelled this material isolate F. Mass isolate F right after grinding. Record Description of final crystals (color, consistency). Record Mass of isolate F post grinding (g).

21. Dry isolate F under reduced pressure or in a vacuum oven at 50° C. Record Description of isolate F (color, consistency). Record Mass of isolate F post drying (g).

Formulation

22. Dissolve isolate F in 2×(mass of isolate F) in mL of petroleum ether. Add this mixture to the flask containing raffinate oil. Stir combined mixture at 55° C. for 20 minutes.

23. Concentrate final oil under reduced pressure. Set vacuum to 0 mtorr and bath to 55° C. Record Mass of flask (g); (should be the same as Step 12). Record Description of final oil (color, consistency. Record Mass of final oil (g).

Example 7. Pre-Process. Concentration of CBD

The following protocol of Example 7 has been used:

1. Add 1000 mL of warm crude oil (55° C.) to a 3000 mL beaker. Record mass (g).

2. Add 500 mL of petroleum ether to the warm crude oil. Stir under gentle heat until the crude oil is dissolved to obtain a homogenous mixture. Use a stir rod and magnetic stirring. Do not heat mixture over 35° C.

3. Let the mixture cool to room temperature over 15 minutes.

4. Place the mixture into an ice bath and cool to 0° C. for 15-60 minutes. Use auto stirrer with a large blade and stir on the lowest speed setting.

5. Add approximately 500 mL of cold petroleum ether to the solid mixture and use the auto stirrer with the small blade to re-blend the mixture. Blend until homogeneous. Note: samples can then be placed into the freezer and left overnight instead of step 6. Placing the samples in the freezer provides slightly better yield (e.g., 5-10% greater).

6. Place the mixture into an ice bath and cool at 0° C. for 60 minutes. Stir by hand with a large metal spatula every 15 minutes, or with an overhead stirrer constantly to homogenize. Alternatively, simply let the mixture cool in an ice bath at 0° C. for 60 minutes.

7. Add approximately 1 L of cold petroleum ether to the filter to prime the filter.

8. Add 0.5 L of cold petroleum ether to the beaker with the mixture. Mix gently in the beaker. Pour the mixture into the filter and stir gently. It should be a light orange/yellow and look like a smoothie. Break up any clumps at this point by pressing them against the side of the filter with the spatula.

9. Place the filter under vacuum. Mix with a large spatula until clumpy light yellow solid remains. It should be a cookie dough like consistency.

10. Remove filter from vacuum. Close the vacuum valve. Add approximately 0.75 L of cold petroleum ether to the filter and stir with a large spatula until the solid is homogenously mixed. It should look like a vanilla milkshake.

11. Place the filter under vacuum. Mix with a large spatula until white remains. It should be a powder like consistency.

12. Remove filter from vacuum. Close the vacuum valve. Add approximately 0.75 L of cold petroleum ether to the filter and stir with large spatula until the solid is homogeneously mixed. It should look like a vanilla milkshake.

13. Place the filter under vacuum. Mix with a large spatula until white remains. It should be a powder like consistency.

14. Using a scoopula or spatula, scrape all the white powder off of the filter into a tared foil tin. Place into vacuum oven at 50° C. and place under vacuum for one hour.

15. Collect the filtrate and concentrate in a 20 L flask for later use.

Example 8. Production THC Removal Method

The following protocol of Example 8 has been used:
Preparation:

1. Pour 10×20 L bottles of diethyl ether into a 55 gallon drum. Seal the lid on this drum tightly.

2. Prepare four gradient tanks:
  a. Prep Tank (PT): 100% petroleum ether (15.9 Gal (60 L) of petroleum ether)
  b. Gradient 1 (G1): 6% diethyl ether in petroleum ether (1.0 Gal (3.6 L) of diethyl ether in 14.9 Gal (56.4 L) of petroleum ether)
  c. Gradient 2 (G2): 15% diethyl ether in petroleum ether (2.4 Gal (9 L) of diethyl ether in 13.5 Gal (51 L) of petroleum ether)
  d. Gradient 3 (G3): 80% diethyl ether in petroleum ether (12.7 Gal (48.0 L) of diethyl ether in 3.2 Gal (12.0 L) of petroleum ether)

3. Insert 5 kg Flash 150 silica column into the steel Flash 150 pressure vessel. Gently tap the column with a rubber hammer to ensure it sits flush with the bottom of the pressure vessel. Close the lid and tightly seal the pressure vessel lid.

4. Ensure all the pressure valves on the entire Flash 150 system are in the closed position.

5. Connect the Flash 150 manifold to the house air. Ensure the house air pressure is no greater than 120 psi using the regulator.

6. Connect the column compression line to the Flash 150 column compression inlet. Turn on column compression and set to 100 psi. Ensure the red pressure indicator is sticking out of the edge of the Flash 150.

7. Connect solvent pressure line A to gradient tank PT via the quick connect pressure inlet. Connect solvent pressure line B to the sample loading chamber via the quick connect pressure inlet. Connect the column inlet line to the solvent outlet valve on the gradient tank PT.

8. Turn on pressure to solvent line A and use the regulator to set the solvent line pressure at approximately 60 psi. Open the solvent outlet valve on gradient tank PT.

9. Turn column inlet so the valve arrow faces solvent line PT. This will enable solvent to flow through the column. (Note: If the column has never been used before, it may take a few minutes for solvent to start flowing from the column outlet valve.)

10. Run gradient tank PT for 17 L (2 CV) to condition the column. Collect all the solvent from this run in a "recycle" solvent container. Solvent should flow out of the column at approximately 2 L per minute. After 17 L of solvent are collected, turn the solvent inlet to the off position. Turn the solvent outlet valve on the gradient tank PT to the off position.

11. Turn the solvent pressure to line A off. Disconnect line A from gradient tank PT and connect line A to gradient tank G1 via the quick connect pressure inlet.

12. Turn the column solvent inlet valve so the valve arrow faces the sample loading vessel line. Increase system pressure to approximately 80 psi. Turn on pressure to solvent line B. Turn on the pressure inlet valve of the sample loading vessel.

13. The sample will begin loading. Watch the sample travel through the clear sample loading tube into the column. Immediately after the entire sample has been loaded onto the column, turn the solvent inlet valve on the column to the off position.

14. Turn off the pressure inlet valve on the sample loading vessel. Decrease the system pressure to 20-30 psi. Disconnect solvent pressure line B from the sample loading vessel and connect solvent pressure line B to gradient tank G2 via the quick connect pressure inlet.

Collection:

15. Gradient Tank 1 (2×10 L fractions, 11×2 L fractions (fractions 1-11)):

a. Ensure the column outlet tube is placed in a 10 L jug labelled Pre1.

b. Turn on solvent pressure line A connected to G1. Ensure the pressure is at 30 psi. open the solvent outlet valve on gradient tank G1. Turn column inlet so the valve arrow faces solvent line G1. Solvent will begin flowing through the column.

c. Collect 10 L (1 CV) of solvent in a 10 L jug A.

d. Collect an additional 10 L (1 CV) in a 10 L jug labelled Pre2. Note: If tallow color is observed before 9 L immediately switch the column outlet tube to 10 L jug B.

e. Begin collecting 2 L fractions in fraction vessels (11 total fractions).

f. After fraction 11, place the column outlet tube in fraction vessel 12 and immediately turn off the column inlet valve connected to solvent line G1. Turn off the solvent outlet valve on gradient tank G1. Turn off solvent pressure line A.

16. Gradient Tank 2 (5×2 L fractions (fractions 12-16)):

a. Turn on solvent pressure line B connected to G2. Ensure the pressure is at 30 psi. Open the solvent outlet valve on gradient tank G2. Turn column inlet so the valve arrow faces solvent line G2.

b. Continue collecting fractions in 2 L portions (5 total fractions).

c. While fractions are being collected, disconnect solvent pressure line A from gradient tank G1 and connect solvent pressure line A to gradient tank G3 via the quick connect pressure inlet.

d. After fraction 16, place the column outlet tube in fraction vessel 17 and immediately turn off the column inlet valve connected to solvent line G2. Turn off the solvent outlet valve on gradient tank G2. Turn off solvent pressure line B.

17. Gradient Tank 3 (4×2 L fractions (fractions 17-20), 2×10 L fractions):

a. Turn on solvent pressure line A connected to G3. Ensure the pressure is at 30 psi. Open the solvent outlet valve on gradient tank G3. Turn column inlet so the valve arrow faces solvent line G3.

b. Continue collecting fractions in 2 L portions (4 total fractions).

c. After fraction 30 switch collection to 10 L jugs.

d. Collect one 10 L fraction labelled Post1. (If solvent is still colored yellow after fraction Post1 collect an additional 8 L fraction labelled Post2.)

e. After fraction Post2/3 turn off the column inlet valve connected to solvent line G3. Turn off the solvent outlet valve on gradient tank G3. Turn off solvent pressure line A.

f. Solvent may continue flowing. Continue collecting solvent in a recycle container until solvent is no longer flowing.

18. Ensure all pressure valves on the system are closed.

19. Ensure connection to house air is closed.

20. Ensure all solvent tanks and the Flash 150 column are completely vented.

21. Clean the sample loading vessel thoroughly with petroleum ether.

Analysis:

22. Run TLC on fractions to determine CBD containing fractions for crystallization, disposal, and recombination.

Raffinate Concentration:

23. Collect raffinate fractions in a tared 20 L flask. Concentrate raffinate fractions under reduced pressure. Set vacuum to 0 mtorr and bath to 55° C. Analyze final dried raffinate with LCMS to determine CBD and THC content.

Crystallization:

24. Tare the 20 L round bottom flask. Label with Date/Batch Number/Initial Tare. Record initial flask tare (g). Record final flask tare (g). Record mass of isolate oil (g).

25. Take the mass of the isolate oil and multiply by 2. The production of this multiplication is the amount of n-hexane that should be added to the 20 L round bottom flask. Record volume of n-hexane (mL).

26. Place the round bottom flask on the rotor at 55 rpm in a hot water bath at 35° C. Do not place under vacuum. Allow to rotate until all of the isolate oil is dissolved and the mixture is homogeneous.

27. Pour the isolate oil mixture into pyrex trays. Each tray should be filled appropriately 0.5 to 1 inches high. Immediately after pouring cover trays with aluminum foil to prevent solvent evaporation.

28. Let the trays cool to room temperature and then lightly seed with isolate crystals. Recover with aluminum foil.

29. Place trays in freezer at −6° C. for approximately 8-10 hours.

30. A layer of crude crystals should have developed. Decant the orange-yellow hexane layer into mother liquor drum.

31. Rinse the crude crystals with approximately 50-100 mL of cold petroleum ether and decant into mother liquor drum.

32. Repeat the rinse.

33. Let the crystals dry at room temperature in fume hood for 1 hour.

34. Crush up the crystals and obtain a mass. Record mass of cyrstals R1 (g).

Second Crystallization:

35. Take the mass of crystals R1 and multiply by 2. The product of this multiplication is the amount of n-hexane that should be added to the 20 L Erlenmeyer flask. Cover the flask lid with a piece of foil to prevent evaporation. Record volume of n-hexane (mL).

36. Stir the n-hexane at 35° C. with a magnetic stir rod until the solvent comes to a boil.

37. Add the crystals from R1 to the hot stirring n-hexane. Stir at 35° C. with a magnetic stir rod until the solvent comes to a boil.

38. Add the crystals from R1 to the hot stirring n-hexane. Stir at 35° C. until the solid is dissolved.

39. Pour the crystallized mixture into pyrex trays. Each tray should be filled approximately 0.5 to 1 inches high. Immediately after pouring cover trays with aluminum foil to prevent solvent evaporation.

40. Let the trays sit at room temperature undisturbed for 8-10 hours.

41. A layer of pristine should have developed. Decant the light-yellow hexane layer into mother liquor drum.

42. Rinse the crude crystals with approximately 50-100 mL of cold petroleum ether and decant into mother liquor drum.

43. Repeat the rinse.

44. Let the crystals dry at room temperature in fume hood for 1 hour. Then break up crystals and transfer to grinder.

45. Grind crystals into a fine powder and transfer to aluminum trays. The powder should completely coat the bottom of the aluminum trays, but the powder layer should be no greater than 0.5 inches.

46. Place the aluminum trays with powder into the vacuum over at 35° C. and place under vacuum for one hour. Record mass of final crystals (from crystals R1) (g). Record mass of final crystals (from pre-run isolate) (g).

Formulation:

47. Dissolve specific amount of CBD isolate in 2×(mass of CBD isolate) in mL of petroleum ether. Add this mixture to the flask containing raffinate oil. Stir combined mixture at 35° C. for 20 minutes.

48. Concentrate final oil under reduced pressure. Set vacuum to 0 mtorr and bath to 35° C. Record mass of flask (g). Record description of final oil (color, consistency). Record mass of final oil (g).

Example 9. Post-Processing. CBG and CBC Isolation

The following protocol of Example 9 has been used:

1. Concentrate the cannabinoids fraction obtained upon column chromatography of the filtrate oil in Example 8 under reduced pressure.

2. Obtain a mass of the cannabinoids oil. For every gram of oil, add 1 mL of hot ethanol.

3. Stir the hot ethanol and cannabinoids oil until a homogeneous mixture is obtained (concentration=0.33 g/mL).

4. Attach a 400 g reverse phase column to the Biotage Isolera. Equilibrate for 3 CV with 80% methanol and 20% distilled water.

5. Inject 24 mL of the cannabinoids oil/ethanol mixture (8 g of cannabinoids oil).

6. Run the following step gradient:
   a. flow rate: 100 mL/min
   b. gradient 1: 80% methanol and 20% distilled water for 4 CV
   c. gradient 2: 85% methanol and 15% distilled water for 7 CV 7. Collect 120 mL fractions for the duration of the run.

8. Run TLC on fractions using 20% diethyl ether and 80% hexane to confirm the identity of cannabinoid fractions. (Fractions collected from 2 CV to 3.5 CV are CBG, fractions collected from 6-9 CV are CBC.)

9. Concentrate the CBG fractions under reduced pressure.

10. Separately concentrate the CBC fractions under reduced pressure.

11. A red oil will remain for the CBG fractions. This can be recrystallized into a solid using 2:1 heptane:CBG.

12. A red oil will remain for CBC fractions. This oil cannot be recrystallized, but is the pure oil form of CBC.

By following this protocol, a hydrate of CBG was obtained. $^1$H NMR (300 MHz, CDCl3) δ 6.26 (s, 2H), 5.50 (s, 2H), 5.27 (t, 1H), 5.06 (t, H), 3.38 (d, 2H), 2.45 (t, 2H), 2.07 (m, 2H), 1.81 (s, 3H), 1.68 (s, 3H), 1.60 (s, 3H), 1.56 (m, 2H) 1.32 (m, 4H), 0.89 (t, 3H) ESMS: 316.24

Each of the documents identified herein is incorporated in its entirety by reference. The foregoing description is illustrative of the disclosure as claimed and is not intended to limit the scope of the disclosure.

We claim:

1. A method of removing one or more cannabis compounds from a cannabis oil, the method comprising:
   obtaining a column packed with a particulate stationary phase;
   adding cannabis oil to the packed column;
   adding a primary eluent to the packed column, wherein the primary eluent added totals between one and eleven column volumes;
   after adding the primary eluent, adding a secondary eluent to the packed column; and
   collecting at least one eluate fraction from the secondary eluent, wherein the at least one eluate fraction comprises at least one cannabinoid.

2. The method of claim 1, wherein the particulate stationary phase is a reverse phase.

3. The method of claim 2, wherein the reverse phase is selected from the group consisting of: C18, C8, C4 and phenyl.

4. The method of claim 1, wherein the primary eluent and secondary eluent are different.

5. The method of claim 4, wherein
   the primary eluent is selected from the group consisting of: 92 vol % petroleum ether and 8 vol % of a mixture of 95% diethyl ether/5% ethanol; 92 vol % pentane and 8 vol % of a mixture of 95% diethyl ether/5% ethanol; 92 vol % n-hexane and 8 vol % of a mixture of 95% diethyl ether/5% ethanol; 96 vol % petroleum ether and 4 vol % of a mixture of 95% diethyl ether/5% ethanol; 96 vol % pentane and 4 vol % of a mixture of 95% diethyl ether/5% ethanol; and 96 vol % n-hexane and 4 vol % of a mixture of 95% diethyl ether/5% ethanol; and
   the secondary eluent is selected from the group consisting of: 70 vol % petroleum ether and 30% of a mixture of 95% diethyl ether/5% ethanol; 70 vol % pentane and 30 vol % of a mixture of 95% diethyl ether/5% ethanol; 70 vol % n-hexane and 30 vol % of a mixture of 95% diethyl ether/5% ethanol; 60 vol % petroleum ether and 40 vol % of a mixture of 95% diethyl ether/5% ethanol; 60 vol % pentane and 40 vol % of a mixture of 95% diethyl ether/5% ethanol; and 60 vol % n-hexane and 40 vol % of a mixture of 95% diethyl ether/5% ethanol.

6. The method of claim 1, wherein the method further comprises monitoring an eluate of the primary eluent or the secondary eluent to detect a presence of one or more cannabinoids.

7. The method of claim 6, wherein the monitoring occurs using at least one of ultraviolet absorption, refractive index, thin layer chromatography, mass spectrometry, and mass selective detection.

8. The method of claim 6, wherein the monitoring detects the presence of CBD in at least a portion of the eluate.

9. The method of claim 8, further comprising:
   pooling at least a portion of eluates from the primary eluent or the secondary eluent to form a pooled eluate;
   evaporating the pooled eluate to form a composition;
   recrystallizing the composition to provide a purified composition comprising at least one cannabinoid.

10. The method of claim 9, wherein the purified composition is greater than 94% purity CBD.

11. The method of claim 1, further comprising:
   prior to adding the cannabis oil to the packed column, diluting the cannabis oil with a non-polar solvent.

* * * * *